United States Patent
Xie et al.

(10) Patent No.: US 9,226,952 B2
(45) Date of Patent: Jan. 5, 2016

(54) NA/K-ATPASE-DERIVED PEPTIDE SRC INHIBITORS AND OUABAIN ANTAGONISTS AND USES THEREOF

(71) Applicant: The University of Toledo, Toledo, OH (US)

(72) Inventors: Zi-Jian Xie, Saline, MI (US); Zhichuan Li, Toledo, OH (US); Joseph I. Shapiro, Toledo, OH (US)

(73) Assignee: The University of Toledo, Toledo, OH (US)

( * ) Notice: Subject to any disclaimer, the term of this patent is extended or adjusted under 35 U.S.C. 154(b) by 31 days.

(21) Appl. No.: 14/195,401

(22) Filed: Mar. 3, 2014

(65) Prior Publication Data

US 2014/0187484 A1 Jul. 3, 2014

Related U.S. Application Data

(62) Division of application No. 13/133,252, filed as application No. PCT/US2009/067845 on Dec. 14, 2009, now abandoned.

(60) Provisional application No. 61/122,205, filed on Dec. 12, 2008.

(51) Int. Cl.
| | |
|---|---|
| *C07K 4/00* | (2006.01) |
| *A61K 38/46* | (2006.01) |
| *C07K 14/47* | (2006.01) |
| *C12N 9/14* | (2006.01) |
| *A61K 38/00* | (2006.01) |

(52) U.S. Cl.
CPC .............. *A61K 38/46* (2013.01); *C07K 14/4703* (2013.01); *C12N 9/14* (2013.01); *A61K 38/00* (2013.01)

(58) Field of Classification Search
CPC ................................ A61K 38/005; C07K 4/00
See application file for complete search history.

*Primary Examiner* — Sheridan Swope

(74) *Attorney, Agent, or Firm* — MacMillan, Sobanski & Todd, LLC

(57) ABSTRACT

A novel Src inhibitor that targets the Na/K-ATPase/Src receptor complex and antagonizes ouabain-induced protein kinase cascades and uses thereof are disclosed.

7 Claims, 19 Drawing Sheets
(8 of 19 Drawing Sheet(s) Filed in Color)

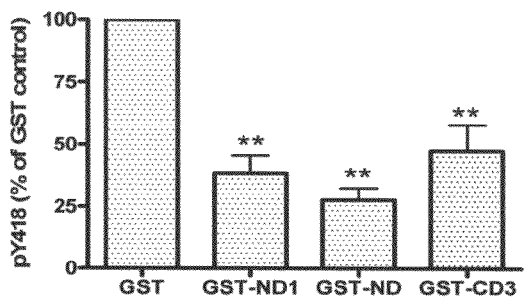
FIG. 2A
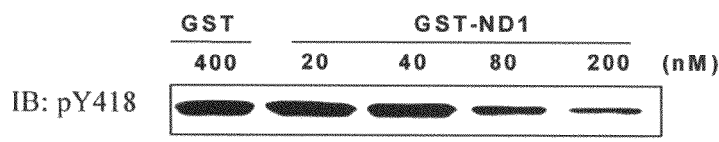
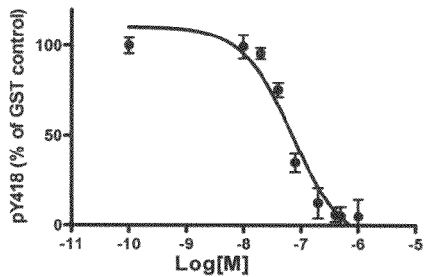
FIG. 2B
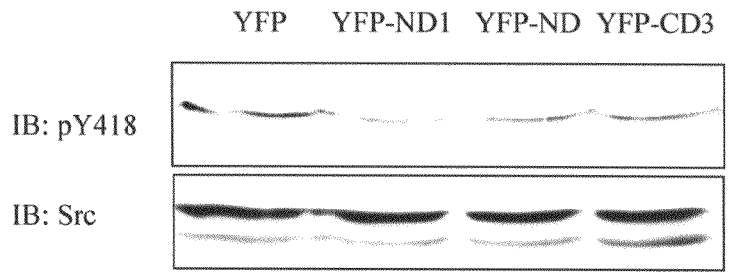
FIG. 2C
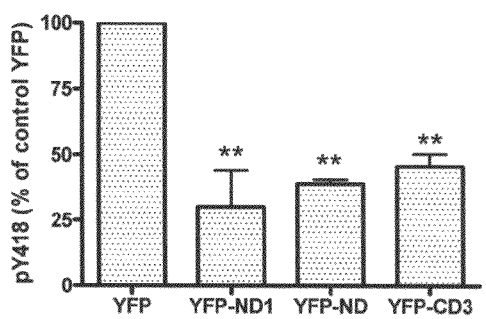
FIG. 2D

```
            P1                                              P3
LTQNR MTVAHMWFDNQ IHEADTTEN QSGVSFDKT SA TWL ALSRIAGLCNRAVFQ ANQEN
                        P2                                  P4
```

FIG. 4A - SEQ ID NO.5

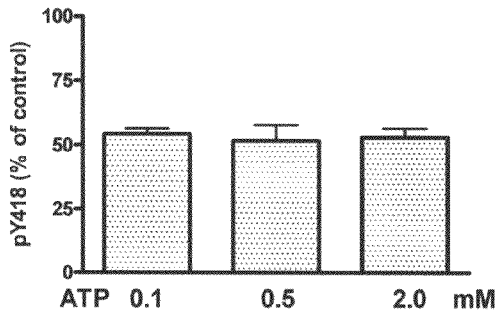
FIG. 4D
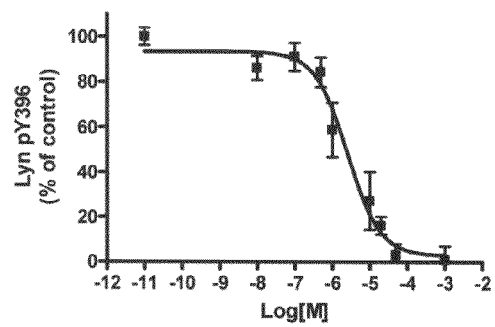
FIG. 4E
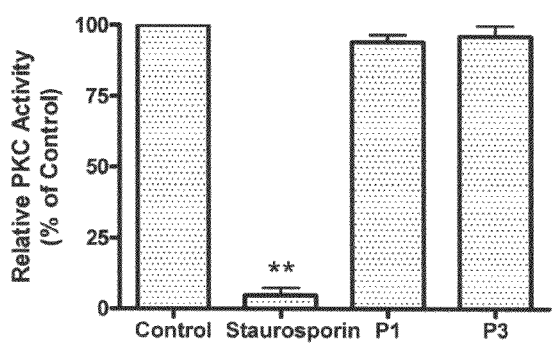
FIG. 4F
| Peptide | Amino acids | |
|---|---|---|
| pC1 | G R K K R R Q R R R P P Q M T V A H M W F D N Q I H E A D T T E N | SEQ ID NO:6 |
| pNaKtide | G R K K R R Q R R R P P Q S A T W L A L S R I A G L C N R A V F Q | SEQ ID NO:7 |
| AP-NaKtide | R Q I K I W F Q N R R M K W K K S A T W L A L S R I A G L C N R A V F Q | SEQ ID NO:8 |
| A1N-NaKtide | K K G K K G K K S A T W L A L S R I A G L C N R A V F Q | SEQ ID NO:9 |
FIG. 5A

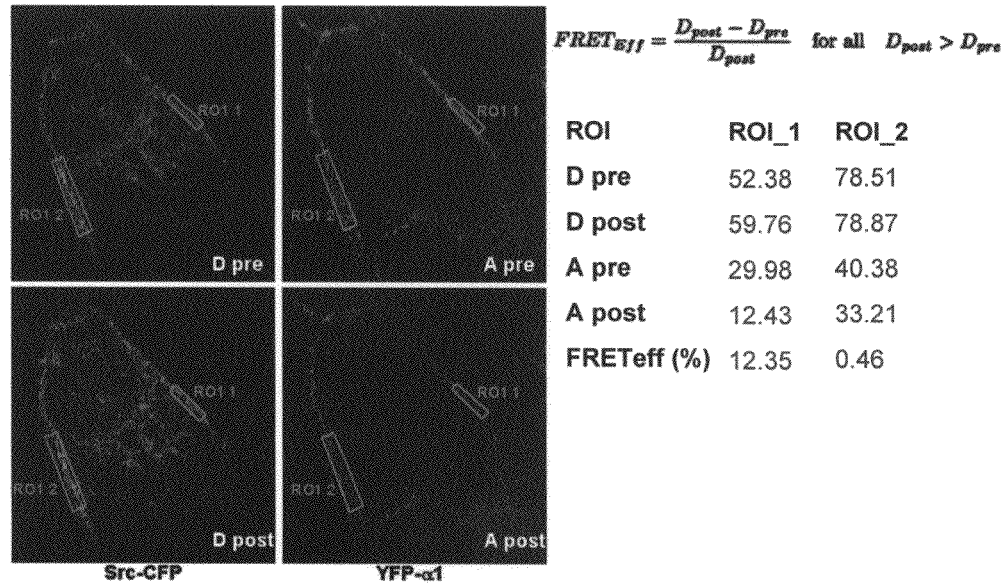
FIG. 6A
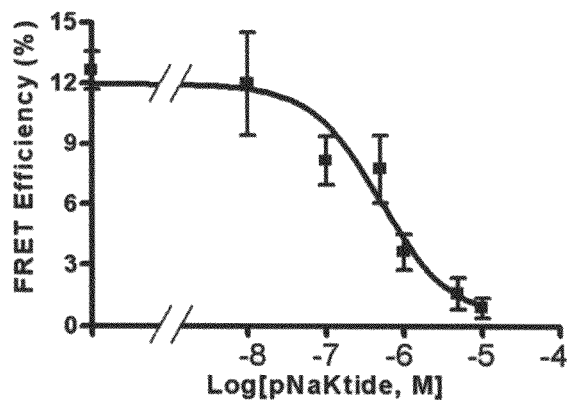
FIG. 6B
| pNaKtide (µM) | 0 | 0.01 | 0.1 | 0.5 | 1 | 5 |
|---|---|---|---|---|---|---|
| Percentage of cells shows FRET | 100 | 100 | 83.3 | 71.4 | 46.2 | 0.0 |
FIG. 6C

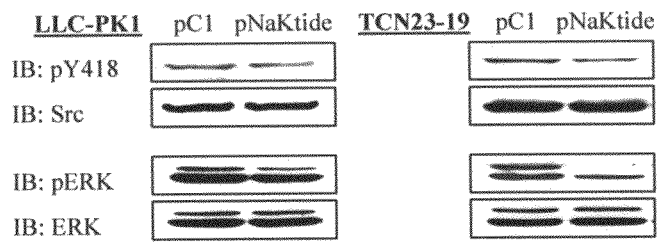
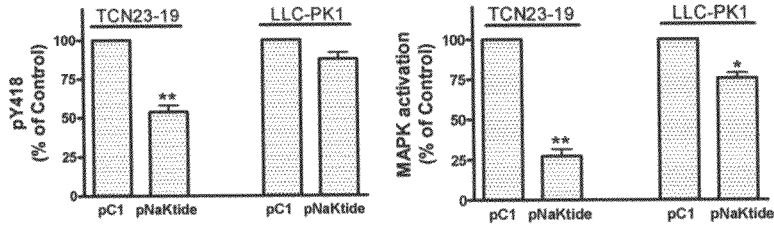
FIG. 7A
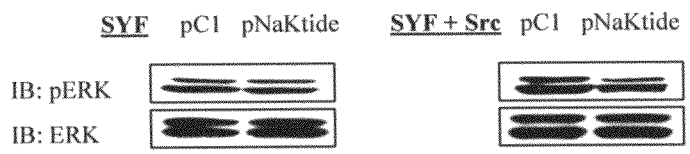
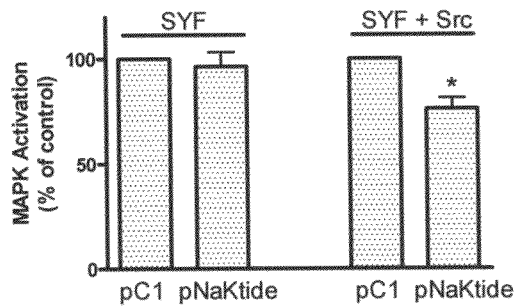
FIG. 7B

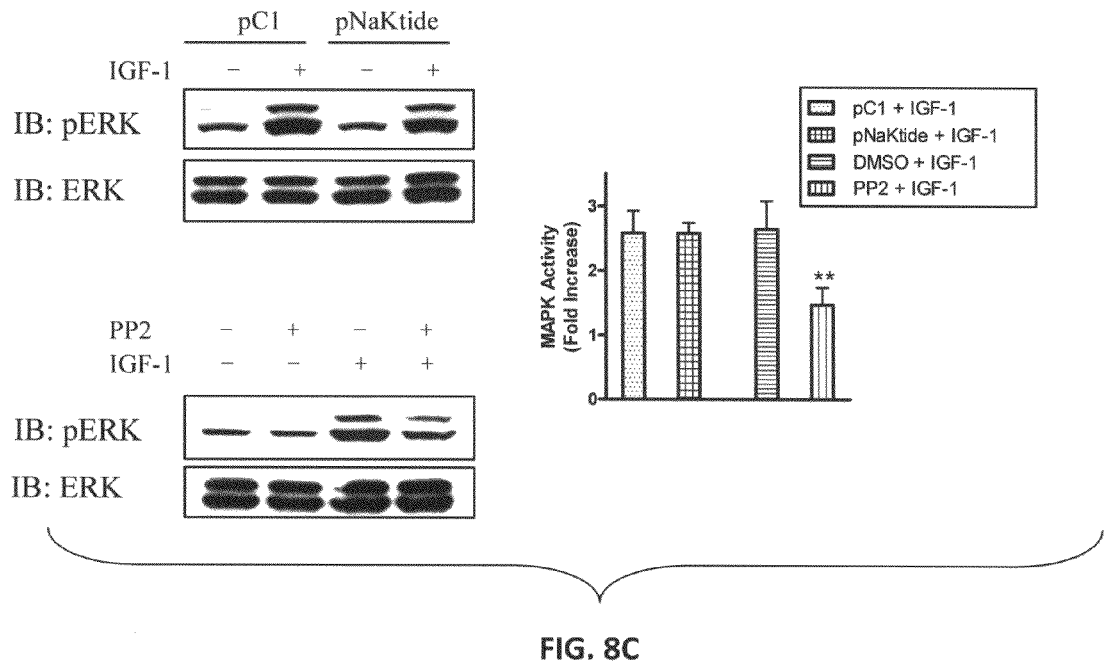

FIG. 8C

Table I. Effects of ND1, pNaKtide and PP2 on Src.

|  | ND1 | NaKtide | pNaKtide | PP2 |
|---|---|---|---|---|
| IC$_{50}$ in vitro | 50nM[a] | 70nM | 4 nM | 5 nM |
| LLC-PK1 | 36 ± 11%[b] | 40 ± 9%[c] | 90 ± 6%[d] | 45 ± 7%[e] |
| Neonatal cardiac myocytes | NA | NA | 93 ± 9%[b] | 42 ± 7%[e] |

GST-ND1 was used *in vitro* for Src activity assay (a). Cells were transfected with either YFP as control or YFP-ND1 for 24 h (b) or pre-treated with 1 μM pNaKtide for 1 h (d) or 1 μM PP2 for 30 min (e). For the NaKtide loading, LLC-PK1 cells were permeabilized with saponin, and then exposed to 1 μM NaKtide for 1h (c). Src pY418 in lysates was analyzed and data are means ± SE, % of control, N=3 to 5. NA, Not available.

FIG. 9

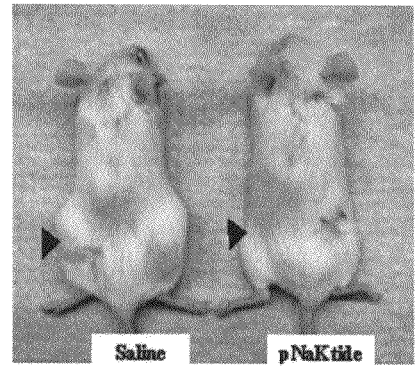
FIG. 15A　　　　　　　　　　FIG. 15B
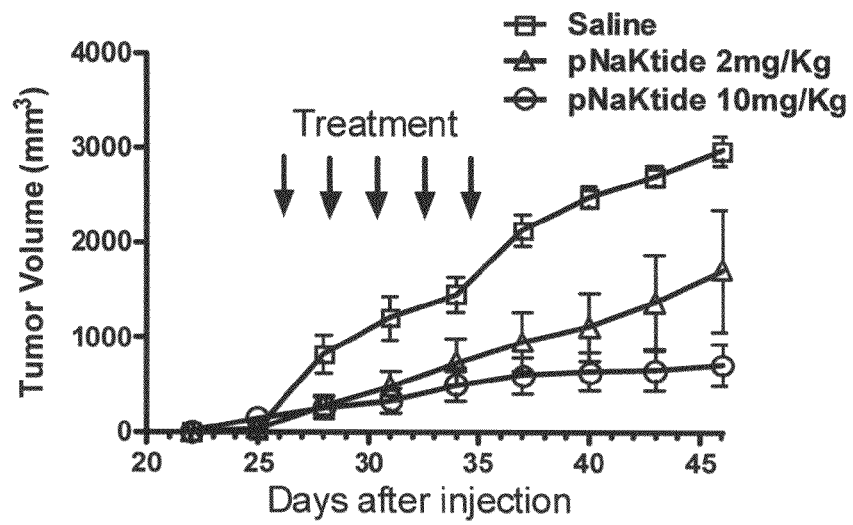
FIG. 15C
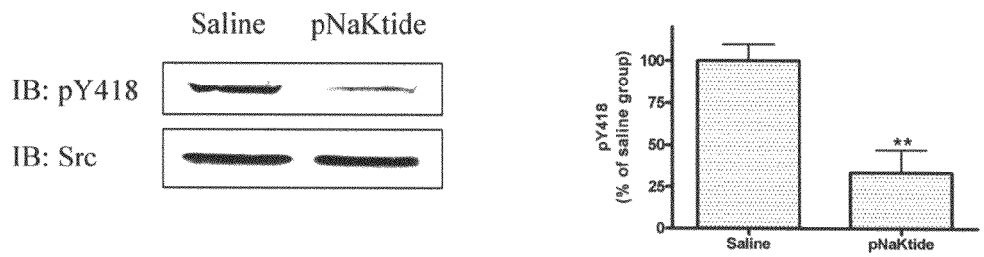
FIG. 15D

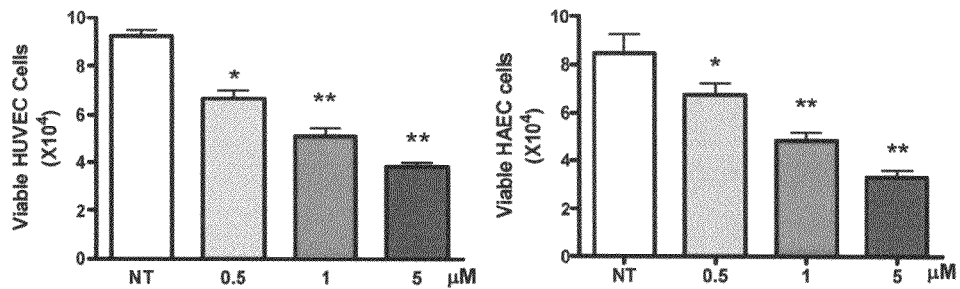
FIG. 16A
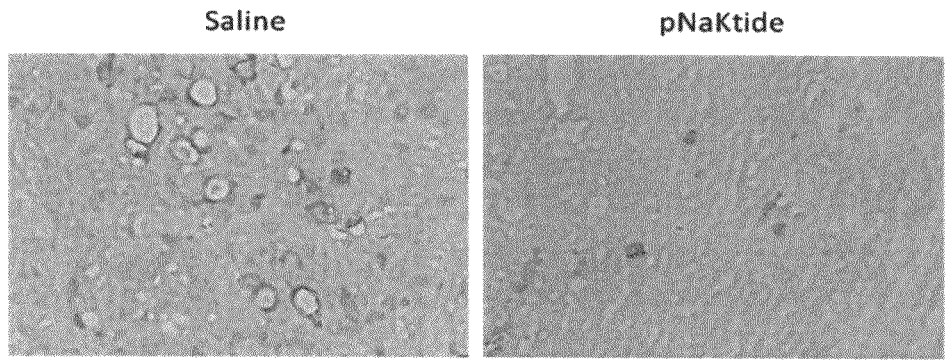
FIG. 16B
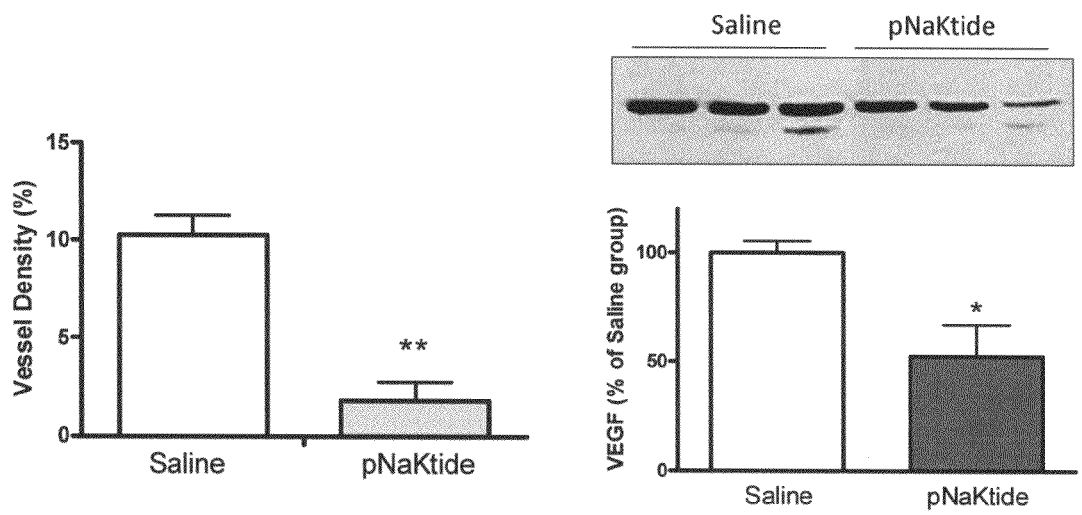
FIG. 16C     FIG. 16D

SEQUENCE LISTING

```
<160> NUMBER OF SEQ ID NOS: 9

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Thr Val Ala His Met Trp Phe Asp Asn Gln Ile His Glu Ala Asp
1               5                   10                  15

Thr Thr Glu Asn
            20

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile His Glu Ala Asp Thr Thr Glu Asn Gln Ser Gly Val Ser Phe Asp
1               5                   10                  15

Lys Thr Ser Ala
            20
```

```
<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Ala Thr Trp Leu Ala Leu Ser Arg Ile Ala Gly Leu Cys Asn Arg
1               5                   10                  15

Ala Val Phe Gln
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Leu Ser Arg Ile Ala Gly Leu Cys Asn Arg Ala Val Phe Gln Ala
1               5                   10                  15

Asn Gln Glu Asn
            20

<210> SEQ ID NO 5
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Leu Thr Gln Asn Arg Met Thr Val Ala His Met Trp Phe Asp Asn Gln
1               5                   10                  15

Ile His Glu Ala Asp Thr Thr Glu Asn Gln Ser Gly Val Ser Phe Asp
            20                  25                  30

Lys Thr Ser Ala Thr Trp Leu Ala Leu Ser Arg Ile Ala Gly Leu Cys
        35                  40                  45

Asn Arg Ala Val Phe Gln Ala Asn Gln Glu Asn
    50                  55

<210> SEQ ID NO 6
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gly Arg Lys Lys Arg Arg Gln Arg Arg Arg Pro Pro Gln Met Thr Val
1               5                   10                  15

Ala His Met Trp Phe Asp Asn Gln Ile His Glu Ala Asp Thr Thr Glu
            20                  25                  30

Asn

<210> SEQ ID NO 7
```

```
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gly Arg Lys Lys Arg Arg Gln Arg Arg Arg Pro Pro Gln Ser Ala Thr
1               5                   10                  15

Trp Leu Ala Leu Ser Arg Ile Ala Gly Leu Cys Asn Arg Ala Val Phe
            20                  25                  30

Gln

<210> SEQ ID NO 8
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Arg Gln Ile Lys Ile Trp Phe Gln Asn Arg Arg Met Lys Trp Lys Lys
1               5                   10                  15

Ser Ala Thr Trp Leu Ala Leu Ser Arg Ile Ala Gly Leu Cys Asn Arg
            20                  25                  30

Ala Val Phe Gln
            35

<210> SEQ ID NO 9
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Lys Gly Lys Lys Gly Lys Lys Ser Ala Thr Trp Leu Ala Leu Ser
1               5                   10                  15

Arg Ile Ala Gly Leu Cys Asn Arg Ala Val Phe Gln
            20                  25
```

NA/K-ATPASE-DERIVED PEPTIDE SRC INHIBITORS AND OUABAIN ANTAGONISTS AND USES THEREOF

CROSS-REFERENCE TO RELATED APPLICATIONS

This application is a divisional application of U.S. patent application Ser. No. 13/133,252 filed Jun. 21, 2011, which is a national stage application filed under 35 USC §371 of international application PCT/US2009/067845 filed Dec. 14, 2009 which claims the benefit of U.S. Provisional Application No. 61/122,205 filed Dec. 12, 2008, the entire disclosures of each of which are expressly incorporated herein by reference for all purposes.

STATEMENT REGARDING FEDERALLY SPONSORED RESEARCH

This invention was made with government support under Grant HL-36573 and Grant GM-78565 awarded by the National Institutes of Health (NIH). The government has certain rights in this invention.

SEQUENCE LISTING

The instant application contains a Sequence Listing which has been submitted via EFS-web and is hereby incorporated by reference in its entirety. Said ASCII copy, created on Dec. 7, 2009, is named 53-50445.txt, and is 3,572 bytes in size.

BACKGROUND OF THE INVENTION

The Na/K-ATPase enzyme is ubiquitously expressed in most eukaryotic cells and is essential for maintaining the trans-membrane ion gradient by pumping $Na^+$ out and $K^+$ into cells. Structurally, the enzyme consists of two non-covalently linked $\alpha$ and $\beta$ subunits Similar to other P-ATPases, including the gastric H/K-ATPase and sarcoplasmic reticulum Ca-ATPase (SERCA), the Na/K-ATPase $\alpha$ subunit has 10 trans-membrane domains with both N- and C-termini located in the cytoplasm. Based on the published crystal structures of both Na/K-ATPase and SERCA, the $\alpha$ subunit consists of several well-characterized domains: actuator (A) domain consists of the N-terminus and the second cytosolic domain (CD2) connected to transmembrane helices M2 and M3; highly conserved discontinuous phosphorylation (P) domain is close to the plasma membrane; and a relatively isolated nucleotide-binding (N) domain. These structures also show a significant movement of A and N domain during the ion pumping cycle. It appears that the A domain rotates while the N domain closes up during the transport cycle, which opens (E1) and closes (E2) the A, N and P domains. Interestingly, these domains have also been implicated in interacting with many protein partners, including inositol 1,4,5-trisphosphate (IP3) receptors (IP3Rs), phosphoinositide 3' kinase (PI3K), phospholipase C-$\gamma$ (PLC-$\gamma$), ankyrin, and cofilin.

Previously, the inventors and others have demonstrated that binding of cardiotonic steroids (CTS) such as ouabain to the Na/K-ATPase stimulates multiple protein kinase cascades. Moreover, knockout of Src abolishes most of these activations. Src, a member of Src family non-receptor kinases, plays an important role in the signal transduction pathways of many extracellular stimuli, i.e., cytokines, growth factors and stress responses and has been considered as a promising target for therapeutic interventions in certain cancers and bone diseases. Several endogenous inhibitors of Src have been documented previously, including c-terminal Src kinase (CSK), CSK-homologous kinase (CHK), Wiscott-Aldrich syndrome protein (WASP), RACK1 and caveolin.

The Na/K-ATPase interacts directly with Src via at least two binding motifs: one being between the CD2 of the $\alpha$1 subunit and Src SH2; and, other involving the third cytosolic domain (CD3) and Src kinase domain. The formation of this Na/K-ATPase and Src complex serves as a receptor for ouabain to provoke protein kinase cascades. Specifically, binding of ouabain to Na/K-ATPase will disrupt the latter interaction, and then result in assembly and activation of different pathways including ERK cascades, PLC/PKC pathway and mitochondrial ROS production. Moreover, this interaction keeps Src in an inactive state. Thus, the Na/K-ATPase functions as an endogenous negative Src regulator. This is consistent with the fact that the basal Src activity is inversely correlated to the amount of Na/K-ATPase $\alpha$1 subunit in both cultured cells and in $\alpha$1 heterozygous mouse tissues. See also, the co-inventors' pending application PCT/US07/023,011, filed Oct. 17, 2007 (Pub. No. WO 2808/054792 on May 8, 2008), claiming priority from U.S. Ser. No. 60/855,482 filed Oct. 16, 2006, which are expressly incorporated herein by reference.

There is still a need to determine the molecular interaction between the Na/K-ATPase and Src in order to then develop novel Src modulators that may be used to antagonize ouabain-induced signal transduction.

Moreover, there is a need for targeting the newly discovered Na/K-ATPase/Src receptor complex to develop novel agonists or antagonists of the receptor so that the receptor function of Na/K-ATPase/Src complex can be either stimulated for treating diseases such as ischemia/reperfusion injury or inhibited for treating diseases such as tissue fibrosis, congestive heart failure, and cancer.

Such a general method would be of tremendous utility in that whole families of related proteins each with its own version of the functional domain of interest could be identified. Knowledge of such related proteins would contribute greatly to our understanding of various physiological processes, including cell growth or death, malignancy, renal/cardiovascular function and immune reactions.

Such a method would also contribute to the development of increasingly more effective therapeutic, diagnostic, or prophylactic agents having fewer side effects.

According to the present invention, just such novel compositions and methods are provided.

SUMMARY OF THE INVENTION

In a broad aspect, there is provided herein a novel Src inhibitor, comprising a composition that targets the Na/K-ATPase/Src receptor complex and antagonizes ouabain-induced protein kinase cascades in one or more cells in need thereof.

In a broad aspect, there is provided herein a novel Src inhibitor, comprising a composition that mimics the Na/K-ATPase-mediated regulation of Src and Src family kinases in one or more cells in need thereof.

In a broad aspect, there is provided herein a novel Src inhibitor, comprising a composition that inhibits Src in vesicular or cytosolic compartments in one or more cells in need thereof.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file may contain one or more drawings executed in color and/or one or more photographs.

Copies of this patent or patent application publication with color drawing(s) and/or photograph(s) will be provided by the Patent Office upon request and payment of the necessary fee.

FIG. 1A: Schematic presentations of different GST-fusion proteins.

FIGS. 1B, 1D: The Coomassie blue staining of purified GST-ND, GST-CD3 and GST-ND1, GST-ND1R, GST-ND2, GST-ND2R.

FIGS. 1C, 1E: Binding of GST-ND and GST-ND1 to Src. Purified His-Src (200 ng) was incubated with 5 μg GST fusion proteins in 0.5% Triton X-100 PBS for 30 min and followed by three washes with the same buffer. A representative Western blot from three independent experiments showed the pulldown products probed with anti-His antibody.

FIGS. 2A-2D: Regulation of Src by ND1.

FIG. 2A: Soluble GST fusion proteins (100 ng) was incubated with recombinant Src (4.5 U) for 15 min in PBS. Src activity was indicated by the phosphorylation of Y418 in the presence of ATP/$Mg^{2+}$.

FIG. 2B: Dose-dependent inhibition of Src by GST-ND1.

FIG. 2C-2D: Effects of YFP-ND1 and other fusion proteins on Src activity in LLC PK1 cells. Cells were transiently transfected with pEYFP or pEYFP-ND1, pEYFP-ND, pEYFP-CD3 plasmids. 24 h after transfection, phosphorylation of Src in the cell lysates was measured by Western blot with anti-pY418 antibody. Representative Western blots and combined data from 3 to 5 independent experiments were shown. ** $p<0.01$ compared with the control.

FIG. 3A: Localization of YFP-ND1 in LLC-PK1 cells. LLC-PK1 cells were transfected with pEYFP-ND1 and localization of YFP-ND1 was detected by confocal microscope. Arrow indicated the plasma membrane localization of YFP-ND1.

FIG. 3B: Lysates from transfected cells were immunoprecipitated with anti-Na/K-ATPase α1 antibody and then analyzed by Western blot using anti-GFP antibody and anti-Na/K-ATPase α1 antibody. A representative Western blot of three separate experiments was shown.

FIGS. 4A-4F: Effect of ND1-derived peptides on Src activity.

FIG. 4A: Sequences of different ND1-derived peptides:

```
peptide 1
                                          [SEQ ID NO: 1]
 . . . MTVAHMWFDNQIHEADTTEN;

peptide 2
                                          [SEQ ID NO: 2]
 . . . IHEADTTENQSGVSFDKTSA;

peptide 3
                                          [SEQ ID NO: 3]
 . . . SATWLALSRIAGLCNRAVFQ;

peptide 4
                                          [SEQ ID NO: 4]
 . . . ALSRIAGLCNRAVFQANQEN;

ND1
                                          [SEQ ID NO: 5]
 . . . LTQNRMTVAHMWFDNQIHEADTTENQSGVSFDKTSATWL
ALSRIAGLCNRAVFQANQEN.
```

Figure 4B:
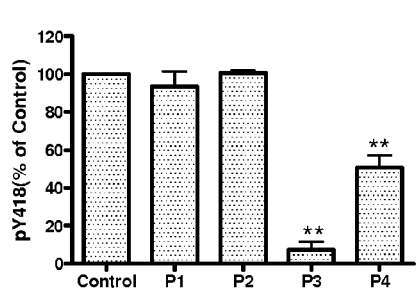

FIG. 4B: Each peptide (1 μM) was incubated with recombinant Src (4.5 U) for 15 min, and then assayed for pY418 as in FIG. 1.

Figure 4C:
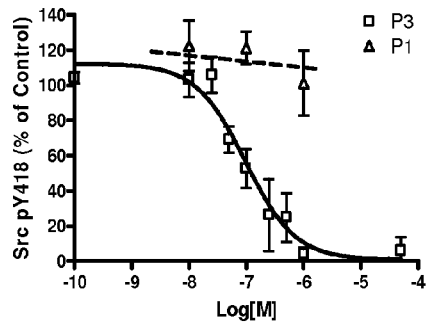

FIG. 4C: Dose-dependent inhibition of Src by the "NaKtide" (peptide 3). Curve fit analysis was performed with GraphPad software.

FIG. 4D: The effect of ATP concentration on the "NaKtide" (peptide 3)-induced Src inhibition. The "NaKtide" (peptide 3) (0.1 μM) was incubated with Src, and then assayed for pY418 in the presence of different concentrations of ATP/$Mg^{2+}$.

FIG. 4E: Effects of the "NaKtide" (peptide 3) on Lyn kinase activity. Recombinant Lyn (100 ng) was incubated with indicated amount of peptide 3 for 15 min, and then assayed for pY396 by Western blot. Curve fit analysis was done with GraphPad software.

FIG. 4F: Effects of the "NaKtide" (peptide 3) on kinase activity of PKC mixture. Quantitative data were presented as mean±SE of at least three independent experiments. ** $p<0.01$ compared with control.

FIGS. 5A-5E: Properties of cell permeable peptides.

FIG. 5A: Sequence information of different peptides:

```
pC1
                                          [SEQ ID NO: 6]
 . . . G R K K R R Q R R R P P Q M T V A H M W F
D N Q I H E A D T T E N;

pNaKtide
                                          [SEQ ID NO: 7]
 . . . G R K K R R Q R R R P P Q S A T W L A L S
R I A G L C N R A V F Q;

AP-NaKtide
                                          [SEQ ID NO: 8]
 . . . R Q I K I W F Q N R R M K W K K S A T W L
A L S R I A G L C N R A V F Q.

A1N-NaKtide
                                          [SEQ ID NO: 9]
 . . . K K G K K G R K S A T W L A L S R I A G L
C N R A V F Q
```

Figure 5B:
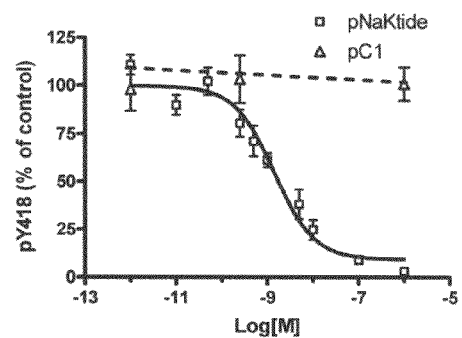

FIG. 5B: Dose-dependent inhibition of Src by the "pNaKtide" and control "pC1". Curve fit analysis was performed by GraphPad software.

Figure 5C:
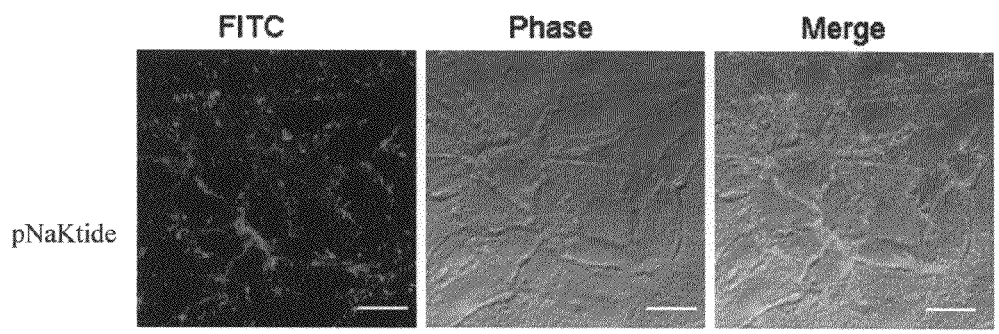
Figure 5D:
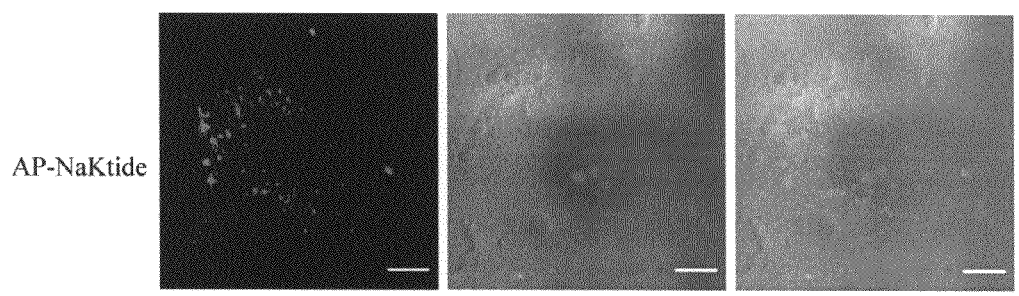

FIG. 5C, 5D: Cell loading analyses of the "pNaKtide" and "AP-NaKtide" in LLC-PK1 cells. Cells were serum-starved for 12 h and then exposed to 1 μM of FITC-pNaKtide or FITC-AP-NaKtide at 37° C. for 60 min. Cells were washed twice with PBS, and analyzed by confocal imaging. The scale bar represents 20 μm.

Figure 5E:
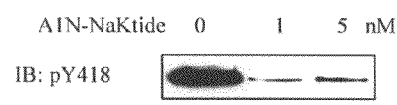

FIG. 5E: Inhibition of Src by "A1N-NaKtide".

FIGS. 6A-6C: Effects of the "pNaKtide" on the formation of Na/K-ATPase/Src complex.

FIG. 6A: LLC-PK1 cells were transfected with EYFP-rat α1 (yellow) and Src-ECFP (cyan). FRET analysis was performed as described herein. Region of Interest 1 (Boxed area marked by ROI 1) was photobleached and analyzed for FRET. The same measurement was done in ROI 2 that was not photobleached.

FIGS. 6B, 6C: The same FRET analyses were conducted in transfected cells pretreated with 1 μM pC1 or different concentrations of "pNaKtide" for 1 h. Average FRET efficiency (FIG. 6B) and percentage of cells (FIG. 6C) showing FRET efficiency (cut-off value is 4.0%) were calculated. At least 20 cells from three experiments were measured for each condition.

FIGS. 7A-7B: Effect of the "pNaKtide" on Src and Src-mediated signaling pathway.

FIG. 7A: Cells were serum-starved for 12 h and were exposed to 1 μM "pC1" or the "pNaKtide" for 1 h. Cell lysates were assayed by Western blot. N=3. * p<0.05; ** p<0.01 compared with control pC1.

FIG. 7B: SYF and SYF+Src cells were exposed to 1 μM "pC1" or the "pNaKtide". Cell lysates were analyzed by Western blot. N=3. * p<0.05 compared with control pC1.

Figure 8A:
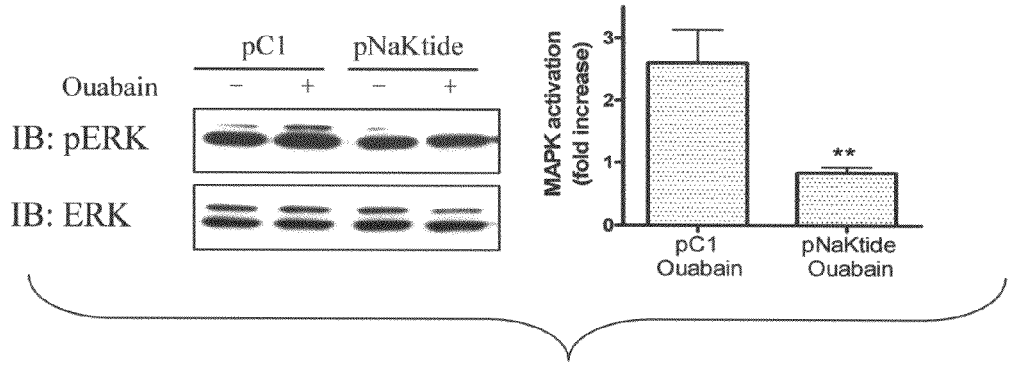
Figure 8B:
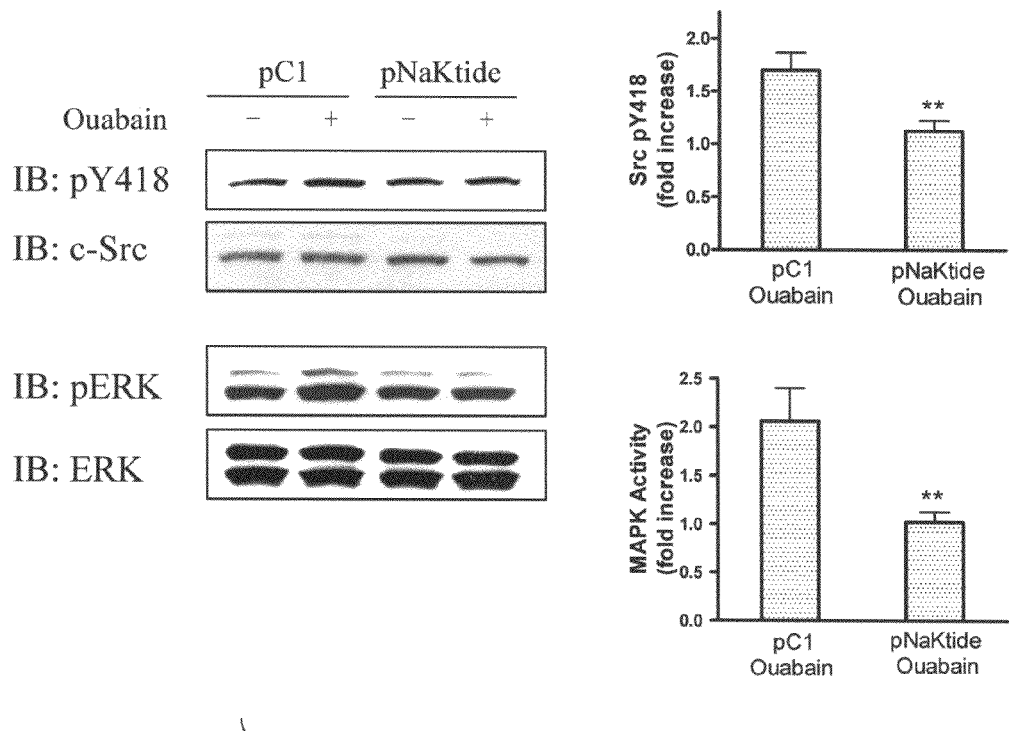

FIGS. 8A-8C: Effect of the "pNaKtide" on ouabain-induced signal transduction.

FIGS. 8A, 8B: LLC-PK1 (FIG. 8A) and primary cultured cardiac myocytes (FIG. 8B) were pre-incubated with 1 μM peptides for 1 h and then exposed to 100 nM (LLC-PK1) or 100 μM (myocytes) ouabain. Cell lysates were analyzed by Western blot. N=3. ** p<0.01 compared with control peptide.

FIG. 8C: Primary cultured cardiac myocytes were pre-incubated with 1 μM peptides for 1 h or PP2 for 30 min, and then exposed to 20 ng/ml IGF-1 for 5 min N=3. ** p<0.01.

FIG. 9: Table 1 showing the effects of ND1, NaKtide, pNaKtide and PP2 on Src.

FIG. 10A-10D: Correlation between Na/K-ATPase α1 amount and Src activity.

Figure 10A:
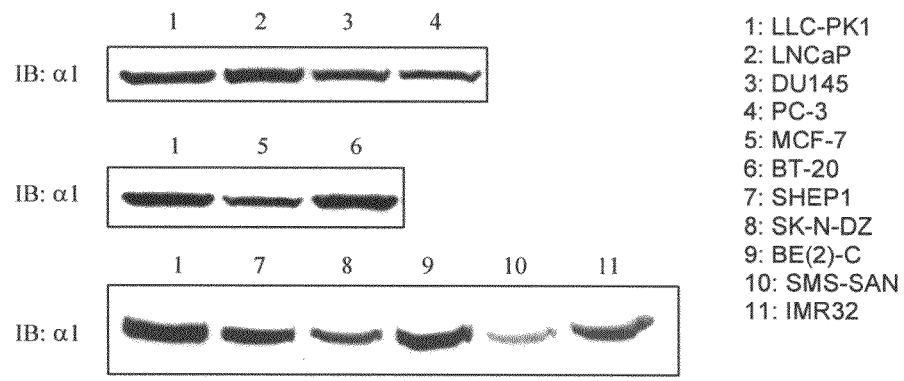

FIG. 10A: Expression level of Na/K-ATPase α1 in different cell lines. Various cells were harvested at 95% density and lysates were analyzed by Western blot with anti-Na/K-ATPase α1 antibody.

Figure 10B:
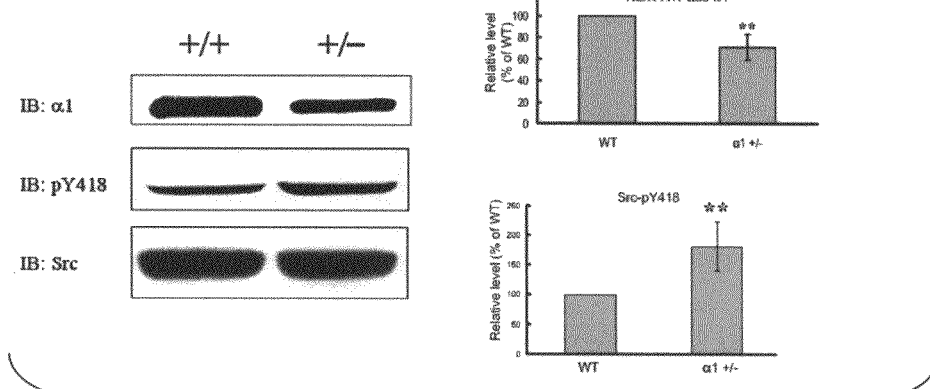

FIG. 10B: Effects of Na/K-ATPase knockdown on Src activity in mouse liver. Liver samples from wild type (WT) and Na/K-ATPase a1knockdown (+/−) mice were assessed by Western blot. N=6. ** p<0.01.

Figure 10C:
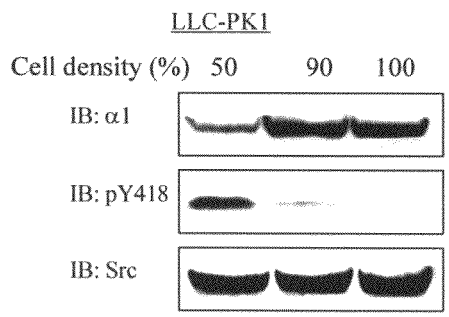
Figure 10D:
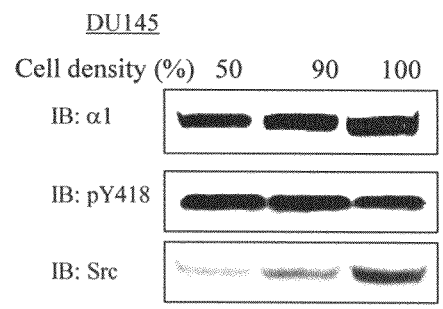

FIG. 10C, 10D: Changes of Na/K-ATPase α1 amount in cells with different densities. Lysates of LLC-PK1 cells (FIG. 10C) and DU145 cells (FIG. 10D) under indicated cell densities were analyzed with anti-Na/K-ATPase al, pY418 and Src antibodies.

Figure 11A:
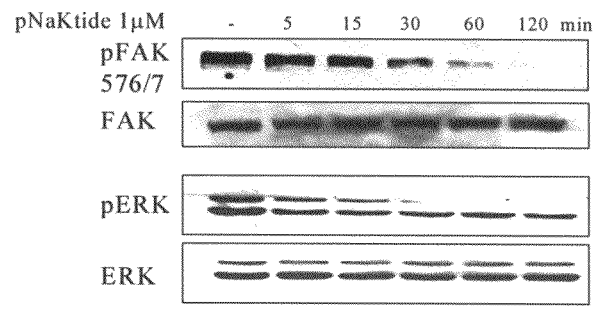
Figure 11C:
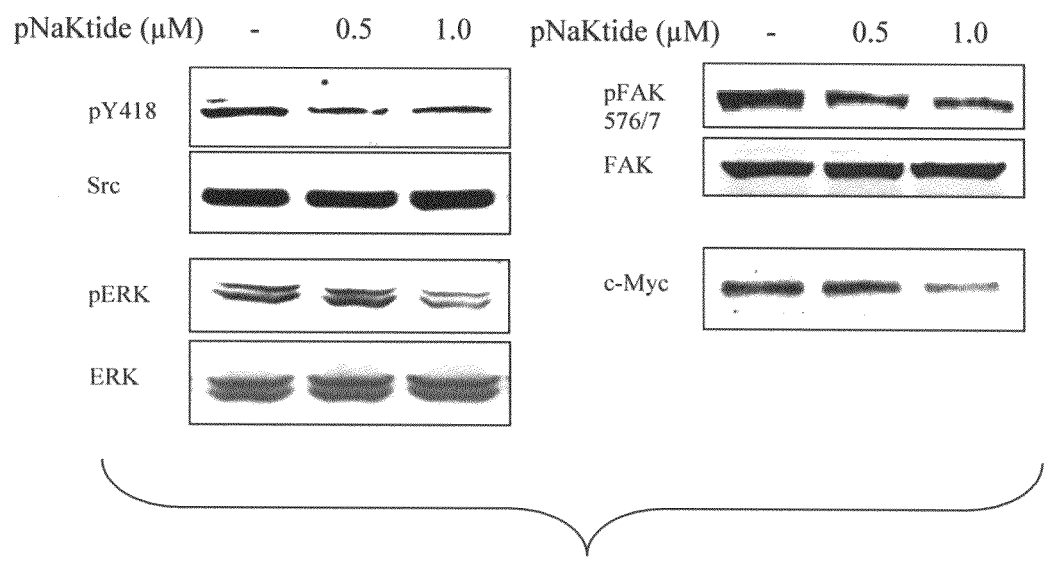
Figure 11B:
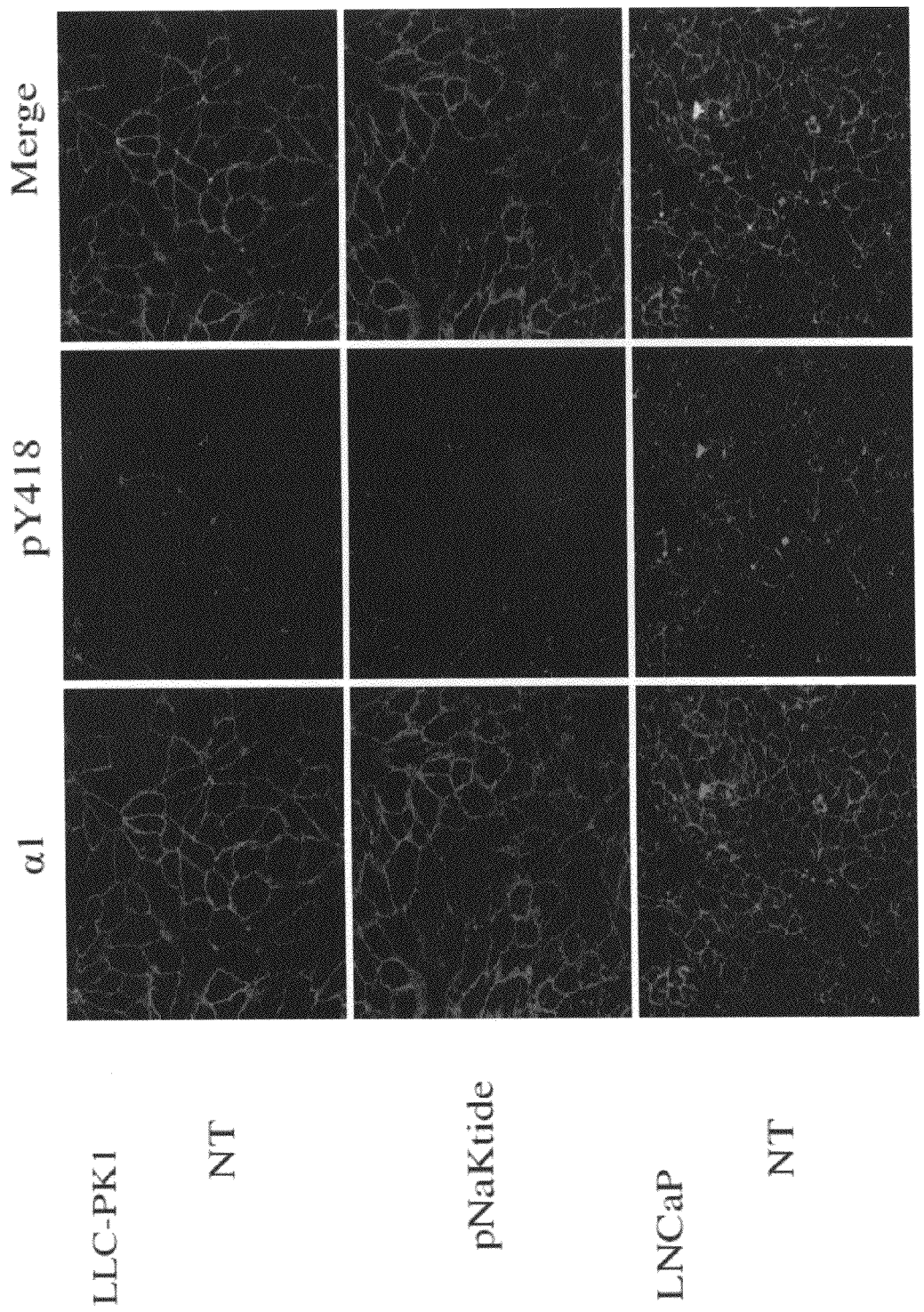
Figure 11B:
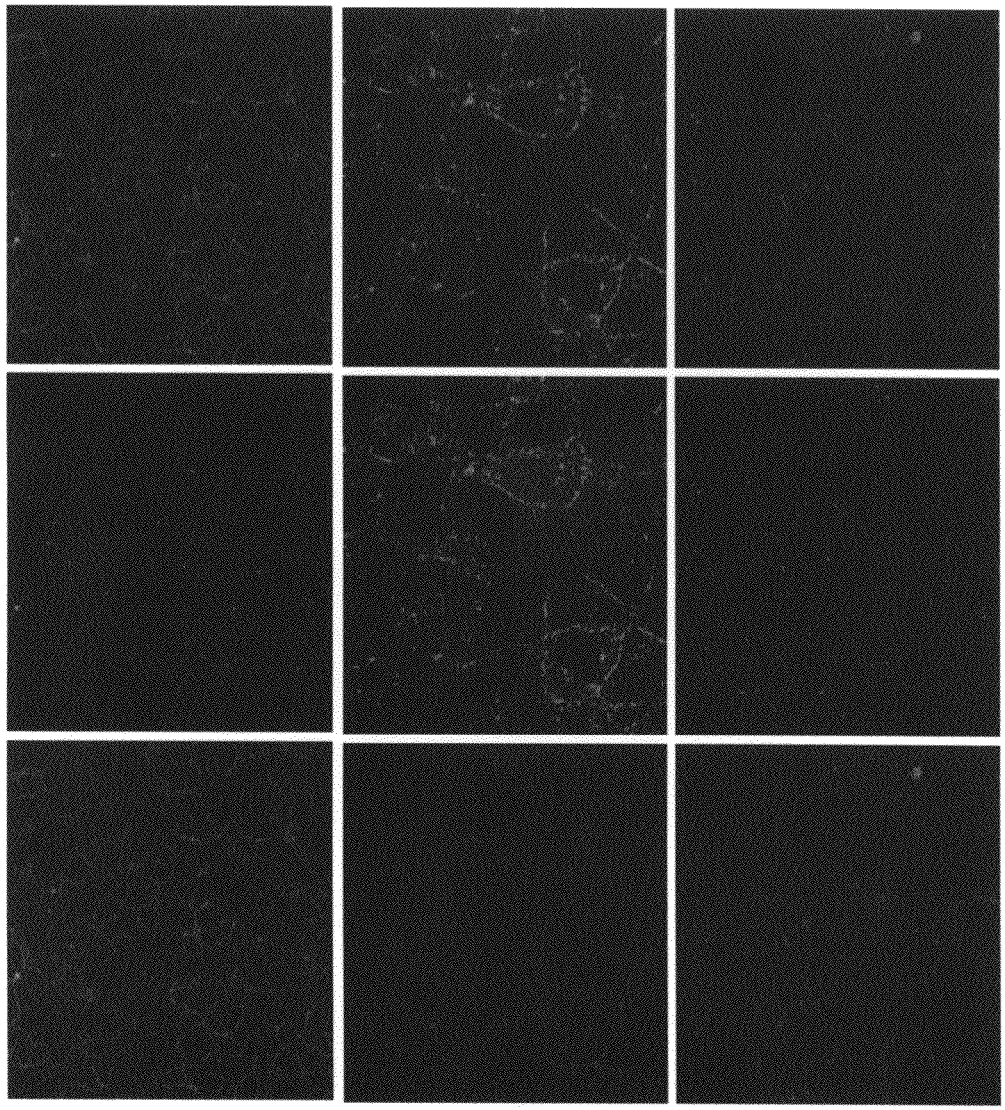

FIG. 11A-11C: Regulation of Src and Src-mediated signaling by "pNaKtide".

FIG. 11A: Regulation of basal FAK and ERK phosphorylation by "pNaKtide". TCN23-19 cells were serum-starved for 12 h and then exposed to 1 μM "pNaKtide" for indicated times. FAK and ERK phosphorylation was assessed by Western blot with anti-pFAK576/7 and anti-phospho-ERK antibodies, respectively.

FIG. 11B: Effect of "pNaKtide" on Src in various cells. Cultured LLC-PK1, LNCaP, and DU145 cells were exposed to 1 μM pNaKtide for 1 h. Then cells were fixed with cold methanol and immunostaining was performed with anti-Na/K-ATPase α1 and anti-pY418 antibodies.

FIG. 11C: Regulation of Src and Src-mediated signaling by "pNaKtide" in DU145 cells. Cell lysates were analyzed by Western blot with antibodies against pY418, phosphor-ERK, pFAK576/7 and c-Myc. Membranes were striped and reprobed with antibodies against Src, ERK, and FAK.

Figure 12:
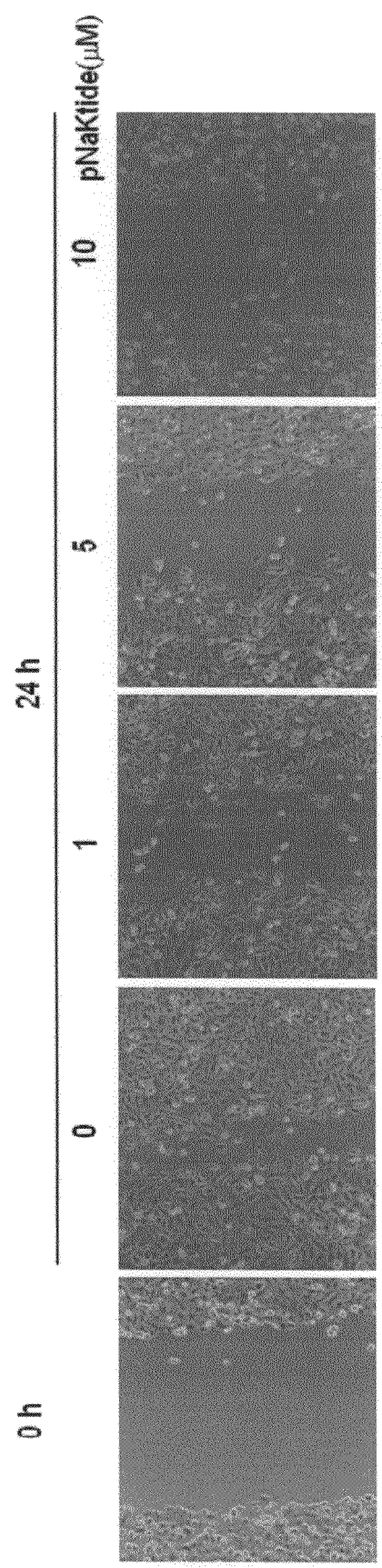

FIG. 12: Effect of "pNaKtide" on prostate cancer cell migration. Scraped wound was introduced on confluent monolayer DU145 cells and the status of wound closure in the absence or presence of "pNaKtide" was monitored after 24 h.

Figure 13A:
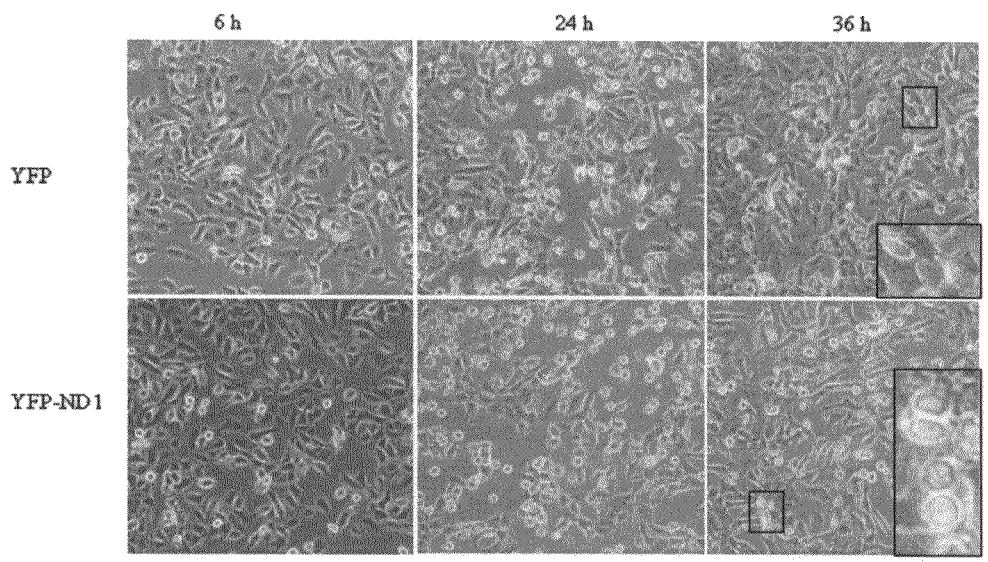
Figure 13B:
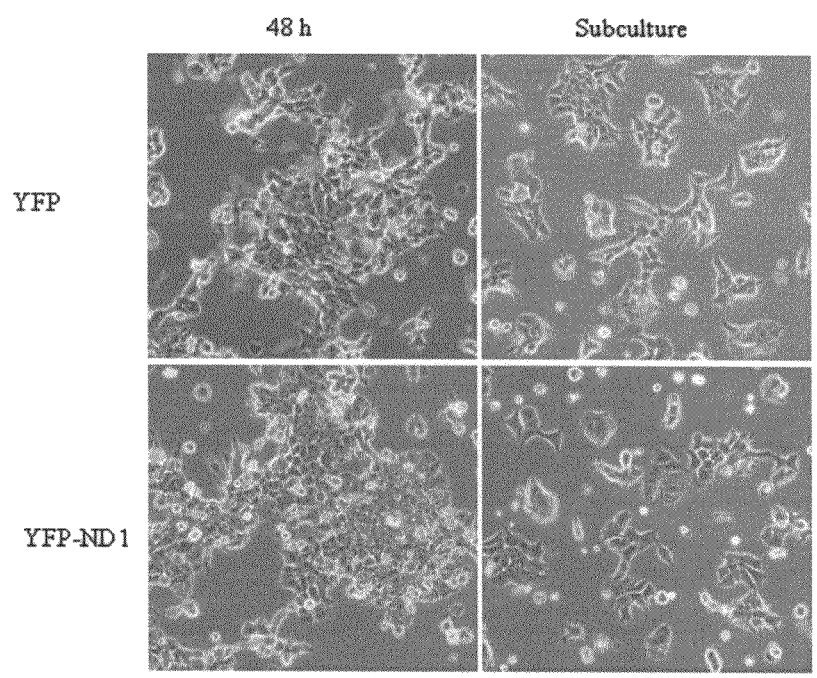

FIG. 13A, 13B: Effect of ND1 overexpression on cell viability in cancer cells. DU145 cells (FIG. 13A) or MCF-7 cells (FIG. 13B) were transiently transfected with plasmid constructs expressing YFP or YFP-ND1 using LipofectAMINE 2000. Fluorescence and phase-contrast images were collected at indicated time after transfection and then merged with SPOT Version 4.6 software (Diagnostic Instruments). Small boxed regions were enlarged and shown in the bottom right boxes. Original magnifications, ×400. The same experiments were repeated at least three times.

FIG. 14A-14D: Effects of "pNaKtide" on cell viability in various cancer cells. N=4. * p<0.05. ** p<0.01.

Figure 14A:
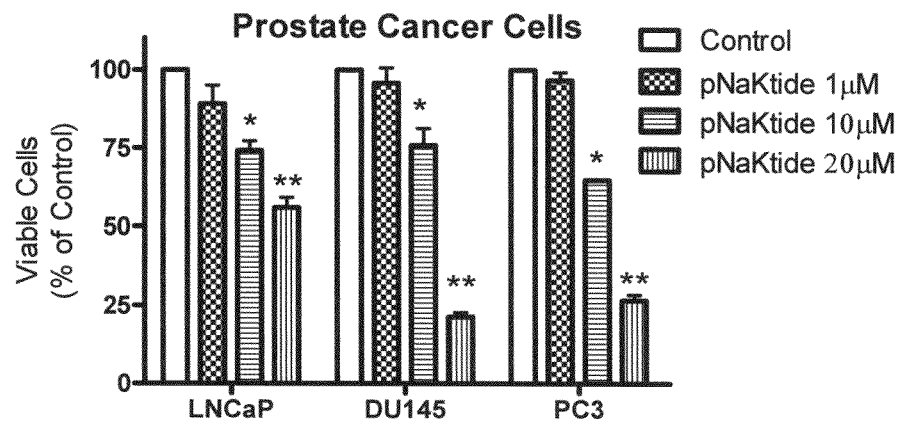

FIG. 14A: "pNaKtide" caused dose-dependent inhibition of cell viability in LNCaP, DU145, and PC-3 prostate cancer cells.

Figure 14B:
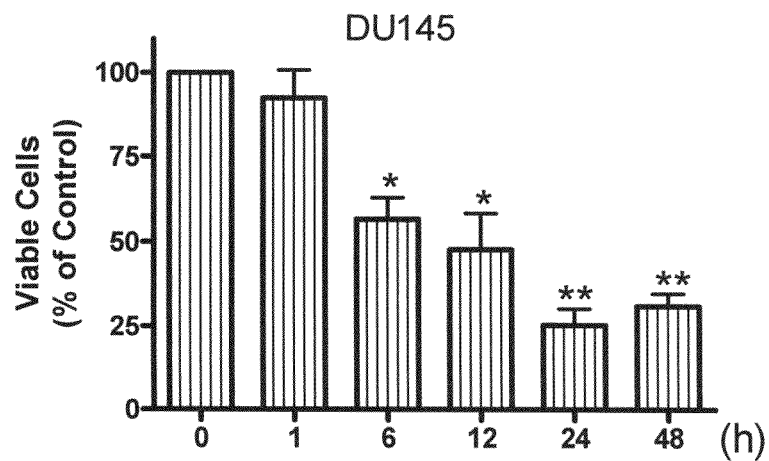

FIG. 14B: Time-dependent effect of "pNaKtide" on DU145 cell viability.

Figure 14C:
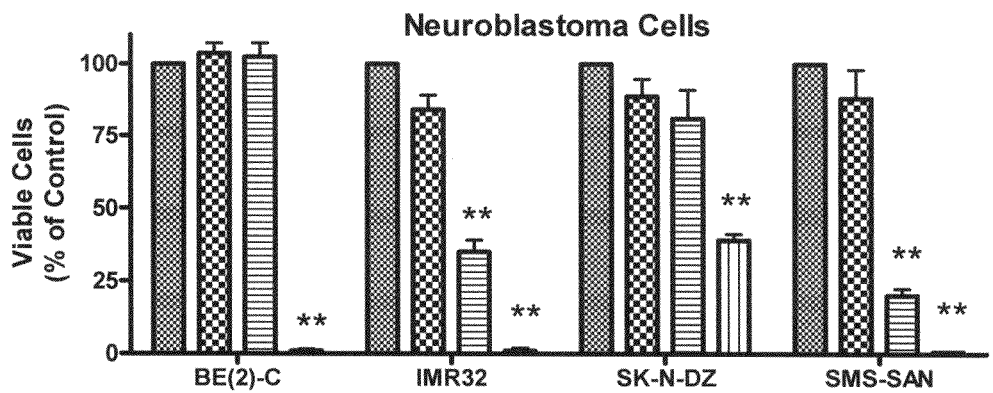
Figure 14D:
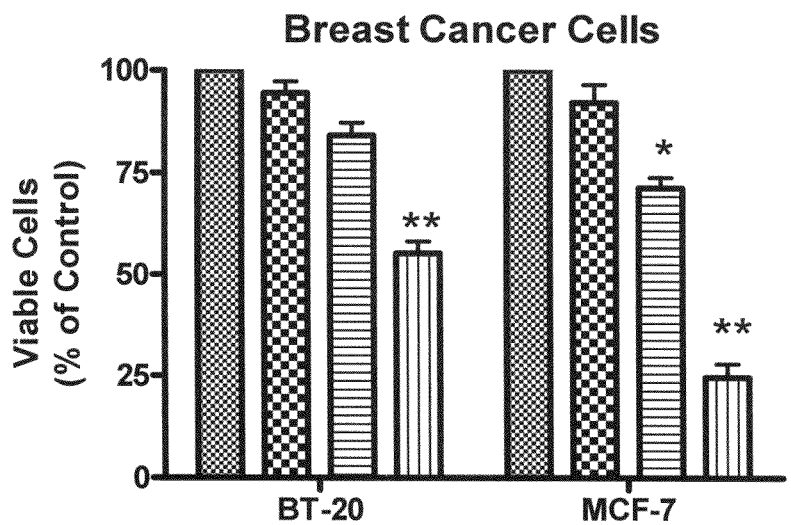

FIG. 14C, 14D: Dose-dependent inhibition of cell viability in neuroblastoma cells (FIG. 14C) and breast cancer cells (FIG. 14D).

FIG. 15A-15D: Effects of "pNaKtide" on the growth of DU145 xenograft tumors. $5 \times 10^6$ DU145 prostate cells were injected subcutaneously in the flank of NOD/SCID mice. Tumor volume was estimated by caliper measurements of the length (L) and width (W) as $V=(L \times W^2)/2$. After tumor volume reaches 100 mm$^3$, mice were treated by injecting different dose of "pNaKtide" formulated in saline.

FIG. 15A: Effect of "pNaKtide" on tumorigenicity of DU145 cells in NOD/SCID mice. Tumors were removed and weighted after mice were sacrificed at 44 days. *, P<0.05. **, P<0.01.

FIG. 15B: Mice bearing xenograft tumors. Arrowheads identify the location of the tumors.

FIG. 15C: Growth of DU145 xenograft tumors in NOD/SCID mice treated with saline or "pNaKtide".

FIG. 15D: Inhibition of Src in "pNaKtide" treated xenograft tumors. After Xenograft tumors were removed and weighted, tumor homogenates were assessed by Western blot. **, P<0.01.

FIG. 16A-16D: Effect of "pNaKtide" on angiogenesis. *, P<0.05. **, P<0.01.

FIG. 16A: Inhibition of endothelial cell proliferation by "pNaKtide". Human Umbilical Vein Endothelial cells (HUVEC) and Human Aortic Endothelial cells (HAEC) cultured on 12-well plates were exposed to "pNaKtide" with indicated concentrations for 72 h. Cell numbers were counted with hemocytometer.

FIG. 16B: Immunohistostaining of CD31 in the formalin-fixed, paraffin-embedded xenograft tumors.

FIG. 16C: Effect on the tumor vessel density by "pNaKtide". The vessel density was calculated as the percent of tumor area occupied by vessels.

FIG. 16D: Expression of VEGF in saline/pNaKtide-treated xenografted tumor homogenates. Tumor homogenates were analyzed by Western blot with anti-VEGF antibody.

DETAILED DESCRIPTION

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture"

[R. I. Freshney, ed. (1986)]; "Immobilized Cells And Enzymes" [IRL Press, (1986)]; B. Perbal, "A Practical Guide To Molecular Cloning" (1984). Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. As appropriate, procedures involving the use of commercially available kits and reagents are generally carried out in accordance with manufacturer defined protocols and/or parameters unless otherwise noted.

This invention is based, at least in part, on the inventors' discovery that the Na/K-ATPase binds and inhibits Src. The inventors now reveal the molecular mechanism of Na/K-ATPase-mediated Src regulation.

In a broad aspect, the invention relates to the generation of a novel peptide Src inhibitor from the Na/K-ATPase α1 subunit that targets to the Na/K-ATPase/Src receptor complex and antagonizes ouabain-induced protein kinase cascades in cultured cells.

The invention is also based, at least in part, on the inventors' discovery that the Na/K-ATPase inhibits Src kinase by binding of the N-terminus of nucleotide binding domain to the Src kinase domain. The inventors herein have now further discovered the identification of a 20 amino acid peptide (NaKtide) that functions as an effective Src inhibitor ($IC_{50}$=70 nM). Unlike small molecular Src inhibitors such as PP2, NaKtide is not an ATP analog, thus represents a novel class of Src inhibitors. Moreover, it does not directly affect PKC and ERK families of serine/threonine kinases and it inhibits Lyn, another Src family tyrosine kinase, with a much lower potency ($IC_{50}$=2.5 μM).

The invention is also based, at least in part, on the inventors' discovery that highly positively charged leader peptide conjugates including HIV-Tat-NaKtide (pNaKtide), Penetratin-NaKtide (AP-NaKtide), α1 N-terminus-NaKtide (A1N-NaKtide) readily enter cultured cells.

The invention is also based, at least in part, on the inventors' discovery, using the functional studies of pNaKtide, that this conjugate can specifically target the Na/K-ATPase-interacting pool of Src and acts as a potent ouabain antagonist in cultured cells.

The invention is also based, at least in part, on the inventors' discovery, using the functional studies of AP-NaKtide, that this conjugate can specifically target the intracellular vesicles and can act as a potent Src inhibitor and ouabain antagonist in cultured cells.

The invention is also based, at least in part, on the inventors' discovery, using the functional studies of NaKtide, that loading the cells with soluble NaKtide by either detergent or HIV-Tat-SS-NaKtide (ssNaKtide) conjugate can produce potent inhibition of cellular Src activity and acts as a potent ouabain antagonist in cultured cells.

The invention is also based, at least in part, on the inventors' discovery, using the functional studies of A1N-NaKtide, that this conjugate can specifically target the intracellular compartments and can act as a potent Src inhibitor and ouabain antagonist in cultured cells.

pNaKtide, unlike PP2, resides mainly in the plasma membrane. Consistently, it affects much less the basal Src activity than that of PP2. AP-NaKtide and A1N-NaKtide reside mainly in vesicles and also have less effect on basal Src activity. On the other hand, ssNaKtide would have significant effect on basal Src as PP2.

pNaKtide is effective in disrupting the formation of Na/K-ATPase/Src receptor complex in a dose-dependent manner. Consequently, it blocks ouabain-induced activation of Src and a down-stream signaling pathway such as ERK1/2 in cultured cells.

Unlike PP2, pNaKtide does not affect IGF-induced ERK activation in cardiac myocytes. Thus, in another broad aspect, the present invention relates to the use of pNaKtide as a ouabain antagonist.

In another aspect, there are provided herein methods of using pNaKtide for probing the physiological and pathological significance of the inventors' discovery of the signaling function of Na/K-ATPase and CTS.

The invention is also based, at least in part, on the inventors' discovery that some cancer cells express less Na/K-ATPase and have higher Src activity.

The invention is also based, at least in part, on the inventors' discovery that pNaKtide and AP-NaKtide can mimic the Na/K-ATPase and inhibit Src and then FAK in cancer cells.

The invention is also based, at least in part, on the inventors' discovery that pNaKtide and AP-NaKtide are effective in inhibiting cancer cell migration.

The invention is also based, at least in part, on the inventors' discovery that pNaKtide can inhibit proliferation of endothelial cells and prevent angiogenesis.

The invention is also based, at least in part, on the inventors' discovery that expression of Src inhibiting YFP-ND1 or addition of either pNaKtide or AP-NaKtide inhibits some cancer cell growth or causes cell death.

The invention is also based, at least in part, on the inventors' discovery that pNaKtide is effective in blocking the growth of xenografted prostate cancer in NOD/SCID mice.

In another broad aspect, there is provided herein a method for inhibiting Src activity or antagonizing CTS-induced signal transduction in a subject in need thereof, comprising administering an effective amount of a peptide derived from Na/K-ATPase or biologically active fragments thereof.

In another aspect, there is provided herein a composition that functions as an effective Src inhibitor, is not an ATP analog, does not directly affect PKC and ERK families of serine/threonine kinases, and inhibits Lyn, a Src family tyrosine kinase, comprising one or more peptides derived from Na/K-ATPase or biologically active fragments thereof.

In another aspect, there are provided herein several highly positively charged leader peptide conjugates of NaKtide which readily enter cells.

In another aspect, there is provided herein a method to target NaKtide to different cellular compartments to achieve cellular compartment-specific inhibition of Src, as exemplified by the following conjugates: HIV-Tat-NaKtide (pNaKtide) to the plasma membrane; Penetratin-NaKtide (AP-NaKtide) and Na/K-ATPase α1-N-terminal-NaKtide (A1N-NaKtide) to vesicles; and HIV-Tat-S-S-NaKtide (ssNaKtide) to the cytosol.

In another aspect, there is provided herein a method for targeting the Na/K-ATPase-interacting pool of Src and acting as a potent ouabain antagonist in one or more cells in need thereof, comprising administering an effective amount of pNaKtide.

In another aspect, there is provided herein a method for targeting the Src in vesicles and acting as a potent Src inhibitor or ouabain antagonist in one or more cells in need thereof, comprising administering an effective amount of AP-NaKtide or A1N-NaKtide.

In another aspect, there is provided herein a method for targeting Src in whole cell and acting as a potent Src inhibitor or ouabain antagonist in one or more cells in need thereof, comprising administering an effective amount of ssNaKtide.

In another aspect, there is provided herein a method for disrupting the formation of Na/K-ATPase/Src receptor complex in a dose-dependent manner, comprising administering an effective amount of one or more peptides derived from Na/K-ATPase or biologically active fragments thereof.

In another aspect, there is provided herein a method for blocking ouabain-induced activation of Src and a downstream signaling pathway such as ERK1/2 in a subject in need thereof, comprising administering an effective amount of one or more peptides derived from Na/K-ATPase or biologically active fragments thereof.

In another aspect, there is provided herein use of one or more peptides derived from Na/K-ATPase or biologically active fragments thereof as a ouabain antagonist.

In another aspect, there is provided herein a method for determining the physiological and pathological significance of the inventors' discovery of the signaling function of Na/K-ATPase and CTS, comprising using one or more peptides derived from Na/K-ATPase or biologically active fragments thereof as a probe.

In another aspect, there is provided herein a Src inhibitor comprising a composition capable of targeting the plasma membrane Na/K-ATPase/Src complex selected from one or more of SEQ ID NOs: 1, 2, 3, 4 and 5, or biologically active fragments thereof.

In another aspect, there is provided herein a composition capable of selectively targeting the Na/K-ATPase-interacting pool of Src and of functioning as an effective ouabain antagonist in one or more cells in need thereof, comprising one or more peptides derived from Na/K-ATPase or biologically active fragments thereof.

In another aspect, there is provided herein a Src inhibitor that is specific to Src, shows no direct effect on PKC family of kinases, comprising one or more of ND1, NaKtide, pNaKtide, AP-NaKtide, A1N-NaKtide, ssNaKtide and biologically active fragments thereof.

In another aspect, there is provided herein a specific ouabain antagonist, comprising one or more peptides derived from Na/K-ATPase or biologically active fragments thereof tagged with a positively charged leader peptide. In certain embodiments, the tagged peptide comprises HIV-Tat or Penetratin or Na/K-ATPase α1 N-terminal peptide or other positively charged leader peptide tagged to NaKtide.

In another aspect, there is provided herein a method for determining the physiology and/or probing the pathological significance of Na/K-ATPase and endogenous CTS, comprising using one or more peptides derived from Na/K-ATPase or biologically active fragments thereof.

In another aspect, there is provided herein a new therapeutic composition for cardiovascular diseases where the Na/K-ATPase/Src receptor is over-stimulated, comprising one or more peptides derived from Na/K-ATPase or biologically active fragments thereof.

In another aspect, there is provided herein a method of inducing cell growth inhibition in a subject in need thereof, comprising administering to the subject a therapeutically effective amount of an inhibitor of Src and a CTS antagonist.

In another aspect, there is provided herein a composition for preventing CTS-provoked signaling pathway, the composition comprising one or more peptides derived from Na/K-ATPase or biologically active fragments thereof.

In another aspect, there is provided herein a method for substantially abolishing ouabain-provoked signaling transduction in the heart in a subject in need thereof, comprising administering an effective amount of one or more peptides derived from Na/K-ATPase or biologically active fragments thereof.

In another aspect, there is provided herein use of one or more peptides derived from Na/K-ATPase or biologically active fragments thereof, in the preparation of a medicament for the treatment of a cancer related disorder or a cardiac disease related disorder.

In another aspect, there is provided herein a pharmaceutical composition comprising one or more peptides derived from Na/K-ATPase or biologically active fragments thereof, and a physiologically acceptable carrier.

In certain embodiments, the composition is adapted for use as a treatment for cardiac hypertrophy, tissue fibrosis and/or congestive heart failure.

In certain embodiments, the composition is adapted for use as a chemotherapeutic agent.

In certain embodiments, the composition is adapted for use as a treatment for a cancer related disorder.

In certain embodiments, the composition is adapted for use as a treatment for a cancer related disorder selected from one or more of prostate cancer, breast cancer, and neuroblastoma.

In another aspect, there is provided herein a method of identifying a candidate compound for the treatment of a disorder associated with one or more of cardiac hypertrophy, tissue fibrosis, congestive heart failure or cancer, the method comprising: providing an assay for detecting an interaction between Na/K-ATPase and Src which inhibits Src activity; conducting the assay with a test compound; and identifying a test compound that is a non ATP-competitive Src inhibitor and a CTS antagonist, wherein a test compound that significantly inhibits the disorder is a candidate compound for the treatment of the disorder.

In another aspect, there is provided herein a method of identifying a candidate compound for the treatment of a disorder associated with one or more of cardiac hypertrophy, tissue fibrosis, congestive heart failure or cancer, the method comprising: providing a model of the disorder; contacting the model with a test compound; detecting in the sample a level of: i) one or more peptides derived from Na/K-ATPase or biologically active fragments and active Src thereof, ii) or Na/K-ATPase or CTS binding; and comparing the level of the peptides and active Src to a reference, wherein a test compound that causes a significant difference in a level of the peptides as compared to the reference is a candidate compound for the treatment of the disorder.

In another aspect, there is provided herein a method of diagnosing a subject with a disorder associated with one or more of cardiac hypertrophy, tissue fibrosis, congestive heart failure or cancer, the method comprising: providing a sample from the subject; detecting in the sample a level of: i) one or more peptides derived from Na/K-ATPase or biologically active fragments and active Src thereof, ii) or Na/K-ATPase or CTS binding; and comparing the level of these parameters to a reference, wherein a significant difference in a level of the peptides as compared to the reference indicates that the subject has the disorder.

In another aspect, there is provided herein a method of evaluating a treatment for a disorder associated with one or more of cardiac hypertrophy, tissue fibrosis, congestive heart failure or cancer, the method comprising: providing a sample from the subject; detecting in the sample a level of: i) one or more peptides derived from Na/K-ATPase or biologically active fragments and active Src thereof, ii) or Na/K-ATPase or CTS binding; and administering one or more doses of a treatment, and comparing the level of the peptides and active Src to a reference, wherein a significant difference in a level of the peptides, as compared to an unaffected individual, as compared to the reference indicates the efficacy of the treatment.

In certain embodiments, the reference represents a level of the peptides prior to administration of the treatment.

In certain embodiments, the sample is from cardiac tissue or a cancer cell of the subject.

In another aspect, there is provided herein a method of determining a subject's risk for development of a complication of a disorder associated with one or more of cardiac hypertrophy, tissue fibrosis, congestive heart failure or cancer, the method comprising: providing a sample from the subject; detecting in the sample a level of: i) one or more peptides derived from Na/K-ATPase or biologically active fragments and active Src thereof, ii) or Na/K-ATPase or CTS binding; and comparing the level of the peptides to a reference, wherein a significant difference in a level of the peptides as compared to the reference indicates the subject's risk of developing the complication.

In another aspect, there is provided herein a method of determining when a treatment for a disorder associated with one or more of cardiac hypertrophy, tissue fibrosis, congestive heart failure or cancer, should be initiated in a subject, the method comprising: providing a sample from the subject; detecting in the sample a level of: i) one or more peptides derived from Na/K-ATPase or biologically active fragments and active Src thereof, ii) or Na/K-ATPase or CTS binding; and comparing the level of to a reference, wherein a significant difference in a level of the peptides as compared to the reference indicates whether the treatment should be initiated.

In certain embodiments, the reference represents a level of Na/K-ATPase peptides or Na/K-ATPase or CTS binding in an unaffected subject.

In another aspect, there is provided herein a method for preventing or treating a condition mediated by a ouabain steroid receptor in a subject, comprising administering one or more peptides derived from Na/K-ATPase or biologically active fragments thereof, and/or an agonist or antagonist thereof.

In certain embodiments, the condition is one or more of cancer, cardiac hypertrophy, tissue fibrosis or congestive heart failure.

In another aspect, there is provided herein a method for identifying one or more of: i) a substance that modulates a ouabain steroid receptor, a Na/K-ATPase receptor and/or a Na/K-ATPase/Src receptor complex, ii) a process mediated by a ouabain steroid receptor, a Na/K-ATPase receptor and/or a Na/K-ATPase/Src receptor complex, iii) degradation of a ouabain steroid receptor, a Na/K-ATPase receptor and/or a Na/K-ATPase/Src receptor complex, iv) a ouabain steroid receptor and/or Na/K-ATPase receptor signaling transduction pathway, v) a condition mediated by a ouabain steroid receptor, a Na/K-ATPase receptor and/or a Na/K-ATPase/Src receptor complex, vi) a steroid receptor transactivation, and/or inhibits or potentiates the interaction of a ouabain steroid receptor, a Na/K-ATPase receptor and/or a Na/K-ATPase/Src receptor complex, comprising assaying for a substance that inhibits or stimulates a ouabain steroid receptor, Na/K-ATPase receptor and/or a Na/K-ATPase/Src receptor complex.

In another aspect, there is provided herein a method for evaluating a substance, comprising: reacting one or more peptides derived from Na/K-ATPase or biologically active fragments thereof and a receptor therefore with a test substance, wherein the peptides and receptor bind to form a complex; and comparing to a control in the absence of the test substance to determine if the substance stimulates or inhibits the binding of the peptides to the receptor.

A method of conducting a drug discovery business comprising: a) providing a method for identifying a substance identified using one or more methods described herein; b) conducting therapeutic profiling of substances identified in step a), or further analogs thereof, for efficacy and toxicity in animals; and c) formulating a pharmaceutical preparation including one or more substances identified in step b) as having an acceptable therapeutic profile.

In certain embodiments, the receptor is a ouabain receptor, a Na/K-ATPase receptor and/or a Na/K-ATPase/Src receptor complex.

In certain embodiments, a part of the peptide consists of a binding domain of the peptide that interacts with a ouabain receptor, wherein the part is the N-terminus of nucleotide binding domain that binds the Src kinase domain.

In another aspect, there is provided herein a method for regulating the Na/K-ATPase/Src receptor complex in a subject comprising inhibiting or stimulating the expression of one or more peptides derived from Na/K-ATPase or biologically active fragments thereof, a complex thereof; or the interactions thereof with a receptor.

In another aspect, there is provided herein a method for identifying one or more conditions selected from: cardiac hypertrophy, tissue fibrosis, congestive heart failure or cancer, in a subject comprising detecting changes in one or more peptides derived from Na/K-ATPase or Na/K-ATPase, CTS binding or biologically active fragments thereof in a sample from the subject.

In certain embodiments, the method comprising: collecting a sample from the subject; measuring the levels of one or more peptides in the sample; and comparing the levels of peptides in the sample to the levels in subjects not having cancer or a cardiac condition.

In certain embodiments, significantly decreased levels in the sample compared to levels in samples from subjects who do not suffer from the condition is indicative of an increased risk of the condition in the subject.

In another aspect, there is provided herein agents, compounds, and substances identified using the methods described herein. The agents, compounds, and substances are useful in the treatment or prevention of a condition mediated by a steroid receptor, including a condition mediated by a ouabain receptor.

In another aspect, there is provided herein antibodies specific for peptides derived from Na/K-ATPase or biologically active fragments thereof.

In another aspect, there is provided herein antibodies labeled with a detectable substance and used to detect proteins or complexes derived from Na/K-ATPase or biologically active fragments thereof in biological samples, tissues, and cells.

In another aspect, there is provided herein antibodies having uses in therapeutic applications, and in conjugates and immunotoxins as target selective carriers of various agents which have therapeutic effects including chemotherapeutic drugs, toxins, immunological response modifiers, enzymes, and radioisotopes.

In another aspect, there is provided herein a pharmaceutical composition adapted for administration to a subject for the prevention or treatment of a condition mediated by a steroid receptor comprising an effective amount of one or more peptides derived from Na/K-ATPase or biologically active fragments thereof, or agonists or antagonists thereof, or an agent, compound or substance identified using a method described herein, and a pharmaceutically acceptable carrier, diluent or excipient.

In another aspect, there is provided herein a pharmaceutical composition adapted for the treatment of a patient suffering from a cardiac or cancer disorder which comprises a therapeutically effective amount of one or more peptides derived from Na/K-ATPase or biologically active fragments thereof, or a pharmaceutically acceptable salt thereof.

In another aspect, there is provided herein a pharmaceutical composition comprising an effective amount of one or more peptides derived from Na/K-ATPase or biologically active fragments thereof or an agonist or antagonist thereof, and an appropriate carrier, diluent, or excipient.

In another aspect, there is provided herein a pharmaceutical composition adapted for administration to a subject for the prevention or treatment of a condition mediated by a steroid receptor, in particular a condition mediated by a ouabain receptor, and an appropriate carrier, diluent, or excipient.

In another aspect, there is provided herein use of peptides derived from Na/K-ATPase, biologically active fragments thereof or agonists or antagonists thereof, for the manufacture of, or in the preparation of a medicament.

In another aspect, there is provided herein a substance for inhibiting ouabain-provoked signal transduction comprising one or more of the peptides, or a complex thereof. In certain embodiments, the complex is substantially cell permeable.

In non-limiting examples, the present invention relates to a composition of matter comprising an amino acid peptide comprising at least ten consecutive amino acid residues of the sequence SATWLALSRIAGLCNRAVFQ [SEQ ID NO: 3], or conservative substitutions of one or more amino acid residues, or substitutions with unnatural amino acids to improve pharmacodynamics or/and pharmacokinetics, wherein the peptide is capable of binding the kinase domain of Src.

Included within the scope of the invention are compositions which further comprise a therapeutically acceptable excipient. In certain embodiments, the amino acid peptide comprises the sequence SATWLALSRIAGLCNRAVFQ [SEQ ID NO: 3].

In other embodiments, the amino acid peptide comprises a sequence selected from the group consisting of: SEQ ID NO: 3; SEQ ID NO: 4; and SEQ ID NO: 5.

In particular embodiments, the amino acid peptide comprises SEQ ID NO 7. In other particular embodiments, the amino acid peptide comprises SEQ ID NO: 8 or SEQ ID NO: 9.

Included within the scope of the invention are nucleic acid sequences encoding a composition as described herein.

Included within the scope of the invention are vectors comprising a nucleic acid sequence as described herein. In certain embodiments, the vector comprises pEYFP.

Included within the scope of the invention are cells comprising a vector as described herein. In certain embodiments, the cell is *E. coli*. In certain embodiments, the cell is mammalian. In certain embodiments, the cell is a tumor cell.

In another aspect, there is provided herein a monoclonal antibody selective for a composition as described herein. In certain embodiments, the monoclonal antibody further comprises a detectable label selected from the group consisting of: radioactive label; chemical label; fluorescent label; an antibody; and a protein.

Included within the scope of the invention are compositions where the composition is capable of affecting a cellular process selected from the group consisting of: antagonizing a CTS-induced protein kinase cascade; upregulating a CTS induced protein kinase cascade; Src inhibition; Src stimulation; Na/K-ATPase mimic; Na/K-ATPase competitive inhibitor; Lyn inhibition; Lyn stimulation; ouabain antagonism; ouabain stimulation; ERK1/2 activation; ERK1/2 inhibition; membrane permeability by sodium ions; membrane permeability by potassium ions. In certain embodiments, the composition is not an ATP analog.

Included within the scope of the invention are compositions which further comprise means to therapeutically permeate plasma membrane.

Included within the scope of the invention are compositions further comprise at least one additional therapeutic composition useful to a treat a disease selected from the group consisting of: cancer; vascular disease; cardiovascular disease; heart disease; prostate cancer; breast cancer; neuroblastoma; cardiac hypertrophy; tissue fibrosis; congestive heart failure; ischemia/reperfusion injury.

In certain embodiments, the composition further comprises a second compound bound with the amino acid peptide in a location other than SEQ ID NO: 3, wherein the second compound is selected from the group consisting of: chemotherapeutic drug; toxin; immunological response modifier; enzyme; and radioisotope.

In certain embodiments, the composition further comprises a second compound bound with the amino acid peptide in a location other than SEQ ID NO: 3, wherein the second compound is selected from the group consisting of: HIV-Tat; Penetratin; and HIV-Tat-S—S; GST.

In certain embodiments, the composition comprises HIV-Tat-SEQ ID NO: 3.

In certain embodiments, the composition comprises a fusion protein, provided that the fusion does not disrupt the at least ten consecutive residues of SEQ ID NO: 3. In certain embodiments, the fusion is with GST.

In another aspect, there is provided herein a method to bind a compound to the kinase domain of Src in a Src-expressing cell, comprising contacting a compound described herein to at least one Src-expressing cell. In certain embodiments, the Src-expressing cell is a mammalian cell.

In certain embodiments, the at least one mammalian cell is a cell selected from the group consisting of: heart cell, liver cell, vascular cell; breast cell; prostate cell; kidney cell; muscle cell; blood cell; and brain cell. In certain embodiments, the at least one mammalian cell is cultured in vitro. In certain embodiments, the at least one mammalian cell is an animal model. In certain embodiments, the at least one mammalian cell is a human.

In another aspect, there is provided herein a method of treating a Src-associated disease in a mammal in need of such treatment, comprising administering a therapeutic composition described herein. In certain embodiments, the Src-associated disease is selected from the group consisting of: cancer; vascular disease; cardiovascular disease; heart disease; prostate cancer; breast cancer; neuroblastoma; cardiac hypertrophy; tissue fibrosis; congestive heart failure; and ischemia/reperfusion injury. In certain embodiments, the mammal is a human. In certain embodiments, the therapeutic composition comprises an amino acid peptide comprising a sequence selected from the group consisting of: SEQ ID NO: 3; SEQ ID NO: 4; SEQ ID NO: 5; SEQ ID NO: 7; SEQ ID NO: 8; and SEQ ID NO: 9.

In another aspect, there is provided herein a method of treating cancer in a mammal in need of such treatment, comprising administering a Src-inhibiting therapeutic composition described herein.

In another aspect, there is provided herein a method of treating vascular disease in a mammal in need of such treatment, comprising administering a Src-inhibiting therapeutic composition described herein.

In another aspect, there is provided herein a method of treating cardiovascular disease in a mammal in need of such treatment, comprising administering a Src-inhibiting therapeutic composition described herein.

In another aspect, there is provided herein a method of treating heart disease in a mammal in need of such treatment, comprising administering a Src-inhibiting therapeutic composition described herein.

In another aspect, there is provided herein a method of treating prostate cancer in a mammal in need of such treatment, comprising administering a Src-inhibiting therapeutic composition described herein.

In another aspect, there is provided herein a method of treating breast cancer in a mammal in need of such treatment, comprising administering a Src-inhibiting therapeutic composition described herein.

In another aspect, there is provided herein a method of treating neuroblastoma in a mammal in need of such treatment, comprising administering a Src-inhibiting therapeutic composition described herein.

In another aspect, there is provided herein a method of treating cardiac hypertrophy in a mammal in need of such treatment, comprising administering a Src-inhibiting therapeutic composition described herein.

In another aspect, there is provided herein a method of treating tissue fibrosis in a mammal in need of such treatment, comprising administering a Src-inhibiting therapeutic composition described herein.

In another aspect, there is provided herein a method of treating congestive heart failure in a mammal in need of such treatment, comprising administering a Src-stimulating therapeutic composition described herein.

In another aspect, there is provided herein a method of treating ischemia/reperfusion injury in a mammal in need of such treatment, comprising administering a Src-stimulating therapeutic composition described herein.

In another aspect, there is provided herein a method to reduce increased basal Src activity in a tumor cell, comprising administering a Src-inhibiting composition described herein to a Src-expressing tumor cell.

In another aspect, there is provided herein a method to inhibit FAK in a tumor cell comprising administering a Src-inhibiting composition described herein to a Src-expressing tumor cell. In certain embodiments, the Src-expressing cell is a TCN23-19 cell.

In another aspect, there is provided herein a method to reduce tumor cell migration in a tumor cell test model, comprising administering a Src-inhibiting composition described herein to a Src-expressing tumor cell.

In another aspect, there is provided herein a method to kill cancer cells when the expression of Na/K-ATPase is reduced, comprising administering a Src-inhibiting composition described herein to a Src-expressing tumor cell having reduced Na/K-ATPase expression.

In another aspect, there is provided herein a method of inhibiting cell growth in a tumor cell line, comprising administering a Src-inhibiting composition described herein to a Src-expressing tumor cell line.

In another aspect, there is provided herein a method which further comprises comparison of the ability of a composition described herein to inhibit cell growth in a tumor cell line to a test compound's ability to inhibit cell growth in the same tumor cell line.

In another aspect, there is provided herein a method of inhibiting prostate tumor cell growth in a prostate tumor cell line, comprising administering a Src-inhibiting composition described herein to a Src-expressing prostate tumor cell line.

In another aspect, there is provided herein a method which further comprises comparison of the ability of a composition described herein inhibiting prostate tumor cell growth in a prostate tumor cell line to a test compound's ability to inhibit cell growth in the same prostate tumor cell line.

In another aspect, there is provided herein a method of inhibiting breast tumor cell growth in a breast tumor cell line, comprising administering a Src-inhibiting composition described herein to a Src-expressing breast tumor cell line.

In certain embodiments, the method further comprises comparison of the ability of a composition described herein inhibiting prostate tumor cell growth in a breast tumor cell line to a test compound's ability to inhibit cell growth in the same breast tumor cell line.

In another aspect, there is provided herein a method of inhibiting neuroblastoma cell growth in a neuroblastoma tumor cell line, comprising administering a Src-inhibiting composition described herein to a Src-expressing neuroblastoma tumor cell line.

In certain embodiments, the method further comprises comparison of the ability of a composition described herein inhibiting neuroblastoma tumor cell growth in a prostate tumor cell line to a test compound's ability to inhibit cell growth in the same neuroblastoma tumor cell line.

In another aspect, there is provided herein a method for screening at least one test composition to determine whether the at least one composition affects Src, comprising: introducing a test composition comprising a modified amino acid peptide of SATWLALSRIAGLCNRAVFQ [SEQ ID NO: 3] to Src, wherein the modification is at least one conservative amino acid substitution; and determining whether the test composition affects Src.

In certain embodiments, the affect is selected from the group consisting of: Src binding; Src inhibition; Src stimulation; Src function; Lyn binding; Lyn function; Lyn inhibition; ouabain antagonism; Na/K-ATPase function; ERK1/2 function; FAK inhibition.

In certain embodiments, the method includes introducing a test composition is accomplished in vitro.

In certain embodiments, the method includes introducing a test composition is accomplished in at least one mammalian cell.

In certain embodiments, the method includes introducing a test composition is accomplished in at least one tumor cell line.

In certain embodiments, the method includes determining whether the composition affects Src is measured by cell growth compared to control.

In certain embodiments, the method includes determining whether the composition affects Src is measured by cell migration compared to control.

In certain embodiments, the at least one mammalian cell is an animal model. In certain embodiments, the animal model is a NOD/SCID mouse. In certain embodiments, determining whether the composition affects Src is measured by tumor growth compared to control. In certain embodiments, the at least one mammalian cell is a human.

In certain embodiments, the method includes determining whether the composition affects Src is measured by tumor growth compared to control.

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference. The following examples are intended to illustrate certain preferred embodiments of the invention and should not be interpreted to limit the scope of the invention as defined in the claims, unless so specified.

EXAMPLE I

Materials.

Chemicals of the highest purity and culture media were purchased from Sigma (St. Louis, Mo.). PP2, a Src kinase inhibitor, and staurosporine, a non-specific PKC inhibitor, were obtained from Calbiochem (San Diego, Calif.). The following antibodies were obtained from Santa Cruz Biotechnology (Santa Cruz, Calif.): monoclonal anti-Src antibody (B12), polyclonal anti-ERK antibody, monoclonal anti-phosphor-ERK antibody, polyclonal anti-CD31 antibody, goat anti-rabbit and goat anti-mouse secondary antibodies. The monoclonal anti-His antibody was from GE Healthcare (Buckinghamshire, England). Polyclonal antibodies against phosphor-Akt (Ser473), Phosphor-FAK (576/7), Akt and FAK were purchased from Cell Signaling Technology (Danvers, Mass.). The polyclonal anti-VEGF antibody and monoclonal anti-α1 antibody (α6F) was obtained from Abcam (Cambridge, Mass.) and the Developmental Studies Hybridoma Bank at the University of Iowa (Iowa City, Iowa), respectively. For purification of GST-fused proteins and His-tagged proteins, Glutathione beads from Amersham Bioscience (Uppsala, Sweden) and ProBond Purification System from Invitrogen (Carlsbad, Calif.) were used respectively. Recombinant human Src and Lyn expressed in Sf9 insect cells for kinase activity assay and IGF-1 expressed in *Escherichia coli* were obtained from Upstate Biotechnology (Lake Placid, N.Y.). Plasmids pEYFP-C1 was purchased from Clontech (Palo Alto, Calif.), and pGEX-4T-1 and pTrc-His A vectors were from Invitrogen (Carlsbad, Calif.). The Optitran nitrocellulose membranes used for Western blotting were obtained from Schleicher and Schuell (Dassel, Germany). All the peptides were synthesized with the purity of 95%. Identity and purity were confirmed by high-performance liquid chromatography-mass spectroscopy.

Plasmid Constructs.

The preparation of plasmid constructs expressing GST fusion proteins were done as described (24). GST-CD3 (amino acid residue 350-785), GST-ND (amino acid residue 379-594), GST-ND2 (amino acid residue 379-475), GST-ND2R (amino acid residue 476-594), GST-ND1 (amino acid residue 379-435) and GST-ND1R (amino acid residue 436-594) expression vectors were constructed based on the sequence of pig kidney Na/K-ATPase α1 subunit. His-tagged Src constructs were generated by excising the corresponding Src cDNA from the GST-Src vector and then inserting them into pTrc-His A vector. pEYFP-ND1, pEYFP-ND and pEYFP-CD3 were made by directional subcloning the corresponding cDNAs from the GST-Src vector into pEYFP-C1 vector. All constructs were verified by DNA sequencing.

Cell Preparation, Culture and Transient Transfections.

Pig kidney proximal LLC-PK1, and mouse fibroblast SYF and SYF+Src cells were obtained from American Type Culture Collection (Manassas, Va.) and cultured in DMEM medium containing 10% fetal bovine serum and penicillin (100 U/ml)/streptomycin (100 μg/ml). Na/K-ATPase alknockdown cells PY-17 and TCN23-19 were generated from LLC-PK1 cells as described. LLC-PK1, PY-17 and TCN23-19 cells were serum-starved for 24 h, whereas SYF and SYF+Src cells were cultured in the medium containing 0.5% FBS for 24 h and used for the experiments. All neuroblastoma cells, breast cancer cells, colon cancer cells, and prostate cancer cells were obtained from American Type Culture Collection and maintained according to the instructions. Transient transfections were performed using LipofectAMINE 2000 (Invitrogen) according to the manufacturer's instructions. Experiments were performed 24 h after transfection.

Primary cultures of neonatal rat cardiac myocytes were prepared as described previously with minor modifications. Myocytes were dispersed from ventricles of 1- to 2-day-old Sprague-Dawley rats by digestion with 0.04% collagenase II (Worthington) and 0.05% pancreatin (Sigma) at 37° C. Non-cardiomyocytes were eliminated by preplating for 1.5 h at 37° C. Myocytes were plated at a density of $8 \times 10^2$ cells/mm$^2$ in 100-mm Corning cell culture dishes in Dulbecco's modified Eagle's medium-M199 (4:1) containing 10% (vol/vol) fetal bovine serum (24 h, 37° C.) and then incubated in serum-free medium for 48 h before experimentation. All research on rats was done according to procedures and guidelines approved by the Institutional Animal Care and Use Committee.

Preparation of Src, Na/K-ATPase, GST-Fused Proteins, and His-Tagged Proteins.

Src, without the first 85 amino acid residues, was purified from sf-9 cells as described and used in the initial binding assays to ensure that Src binds to the Na/K-ATPase. In the Src phosphorylation experiment, purified recombinant full-length Src from Upstate Biotechnology was used. Na/K-ATPase was purified from pig kidney outer medulla using the Jorgensen method as we previously described and the preparations with specific activities between 1200 and 1400 μmol Pi/mg/h were used. GST-fused proteins or His-tagged proteins were expressed in *Escherichia coli* BL21 (Invitrogen) and purified using glutathione beads or ProBond Purification System (Invitrogen). Soluble GST-fused proteins were eluted from the glutathione beads with elution buffer [10 mM reduced glutathione, 0.1% Triton X-100, 50 mM Tris-HCl, (pH8.0)] and then dialyzed in the buffer containing 0.1% Triton X-100, 50 mM Tris-HCl (pH8.0) to remove remnant glutathione.

In Vitro GST Pulldown Assay.

GST pulldown assay were performed as following: 5 μg GST-fused proteins were conjugated on glutathione beads and incubated with 100 ng purified his-Src in 500 μl PBS in the presence of 0.5% Triton X-100 at room temperature for 30 mM The beads were washed with the same buffer for four times. The bound his-Src was resolved on 10% SDS-PAGE and detected by Western blot with anti-His antibody.

Kinase Activity Assay of Src and Lyn.

To determine how Na/K-ATPase constructs or peptides affect Src/Lyn kinase activity, the purified Src (4.5 U) or Lyn (20 ng) was incubated with different amount of the purified GST-fused Na/K-ATPase constructs or peptides in PBS for 30 mM at 37° C. Afterward, 2 mM ATP/Mg$^{2+}$ was added. The reaction continued for 5 mM at 37° C. and was stopped by addition of SDS sample buffer. Afterward, the Src pY418 and Lyn pY396 were measured by anti-pY418 antibody to indicate Src/Lyn activation. For the Src activity assay in TCN23-19 cells and primary rat neonatal cardiac myocytes, cells were lysed in ice-cold RIPA buffer containing 1% Nonidet P40, 0.25% sodium deoxycholate, 150 mM NaCl, 1 mM EDTA, 1 mM phenylmethylsulfonyl fluoride, 1 mM sodium orthovanadate, 1 mM NaF, 10 μg/ml aprotinin, 10 μg/ml leupeptin, and 50 mM Tris-HCl (pH 7.4). Cell lysates were cleared by centrifugation at 16,000×g for 15 mM, and the supernatants were separated by SDS-PAGE (60 μg/lane) and transferred to an Optitran membrane and were analyzed with anti-pY418 antibody. The pY418 signal was detected using the enhanced chemiluminescence kit (Pierce) and quantified using a Bio-Rad GS-670 imaging densitometer as we previously described.

PKC Kinase Activity Assay.

Activity of PKC was measured by PepTag phosphorylation assay for non-radioactive detection of PKC (Promega) as described in the product instruction. Briefly, 40 ng PKC were incubated for 30 min at 30° C. with the reaction mixture containing 5 µl reaction buffer, 5 µl PepTag C1 (0.4 µg/µl), 5 µl PKC activator solution, 1 µl peptide protection solution and 10 µM staurosporine or peptide. Then the reaction mixture was subjected to electrophoresis on a 0.8% agarose gel at 100 V for 20 min. After electrophoresis, negatively-charged phosphorylated PepTagC1 peptide migrated toward the anode (+), while non-phosphorylated PepTagC1 peptide migrated toward cathode (−). Percentage of the phosphorylated PepTagC1 was an indicator of the PKC activity.

Immunoblot Analysis.

Following the indicated treatment, the incubation medium was rapidly replaced with ice-cold PBS. The washed cells were then lysed in ice-cold RIPA buffer, and subjected to Western blot analysis with anti phosphor-Akt (Ser473), phosphor-MAPK and phosphor-FAK (Tyr576/577) antibodies as described above. Then the same membrane was stripped and reprobed with anti Akt, MAPK and FAK antibodies respectively.

Image Analysis with Confocal Fluorescence Microscope.

Cells cultured on coverslips were subjected to the indicated treatment. Then cells were washed twice with PBS and fixed for 15 min with methanol prechilled at −20° C. The fixed cells were then rinsed with PBS three times and blocked with 200 µl of Image-iT FX signal enhancer (Invitrogen) for 30 min at room temperature. The cells were washed again and incubated with anti-pY418 antibody in PBS containing 1% bovine serum albumin for 1 h at room temperature. After three washes with PBS, the cells were incubated with Alexa Fluor-conjugated anti-rabbit secondary antibody (Invitrogen). Image visualization was performed using a Leica DMIRE2 confocal microscope (Leica, Mannheim, Germany). Leica confocal software was used for data analysis.

Localization Analysis of pNaKtide in Live Cells.

Cells were cultured on coverslips and then subjected to the indicated treatment of FITC-pNaKtide at 37° C. Cells were washed twice with PBS and localization of pNaKtide was assessed by directly monitoring FITC fluorescence with Olympus fluorescence microscopy (Olympus).

Cell Viability Assay.

After confluence reaches about 60%, cells were exposed to peptides with indicated concentration and time. Cells were then trypsinized and the cell suspensions were mixed with trypan blue at room temperature for 5 m. The numbers of viable cells were counted with hemocytometer.

Wound Closure Assay.

DU145 cells were seeded in 6-well plates in growth medium containing 10% fetal bovine serum. The cells were allowed to grow to confluent monolayer. The wound-induced migration was triggered by scraping the cells with a plastic pipette tip. The cells were then were treated with or without pNaKtide at different concentrations. The wound was imaged immediately (0 h) and at 24 h with an inverted phase-contrast microscope with a ×10 objective.

Establishment of DU-145 Xenograft Tumors in NOD/SCID Mice.

NOD/SCID mice nude mice (NCI) were housed in laminar airflow cabinets under pathogen-free conditions with a 12 h light/12 h dark schedule and fed autoclaved standard chow and water. Xenografts of DU145 were initiated by subcutaneous injection of $5\times10^6$ DU145 cells into the left and right flanks of female nude mice at age of 4-6 weeks. Tumor volume was estimated by caliper measurements of the length (L) and width (W) as $V=(L\times W^2)/2$. Treatment was started after tumors reached an average volume of 100 mm$^3$ Mice were injected subcutaneously near the tumor site with pNaKtide in saline at the dose of 2 mg/kg and 10 mg/kg (body weight) every other day for one week. All research on NOD/SCID mice was done according to procedures and guidelines approved by the Institutional Animal Care and Use Committee of University of Toledo Health Science Campus.

Analysis of Data.

Data are given as the mean±SE. Statistical analysis was performed using the Student's t test, and significance was accepted at $p<0.05$.

Results

Figure 1A:
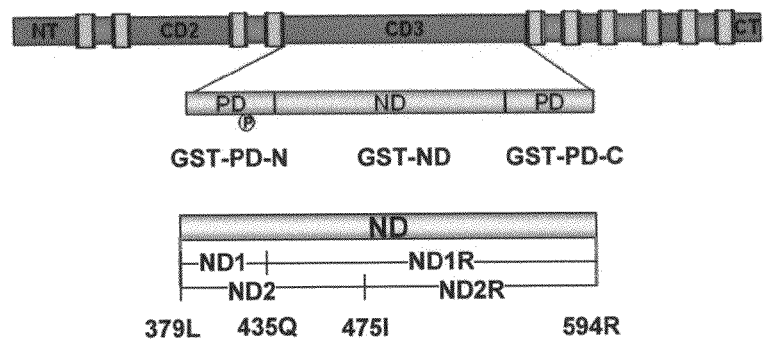
FIGS. 1A-1E: Identification of the N-terminus of the N-domain of the Na/K-ATPase α1 subunit as a Src-interacting motif.
Figures 1B, 1C:
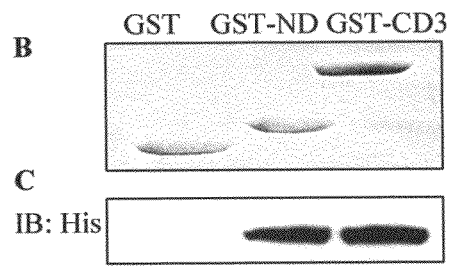
Figure 1D:
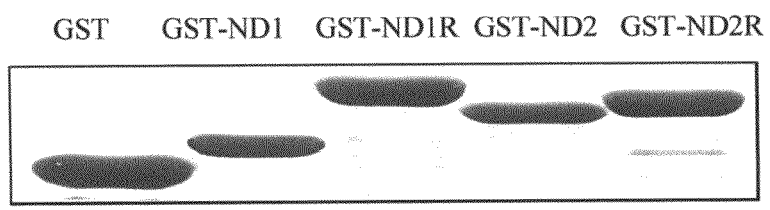

Identification of ND1 as a Src-Interacting Domain from the Na/K-ATPase α1 Subunit:

The CD3 interacted and inhibited Src. As depicted in FIG. 1A, the Na/K-ATPase CD3 consists of both P and N domains. The 3D structure of Na/K-ATPase indicates that the N domain is exposed, whereas the P domain is relatively close to the membrane. Thus, while not wishing to be bound by theory, inventors herein now believe that the N domain interacts with the Src kinase domain. To test, the inventors constructed GST-ND and tested whether it binds the purified His-Src. GST-CD3 was used as a positive control whereas purified GST served as a negative control. Pull-down analyses confirmed that the N domain of α1 subunit interacted with Src (FIG. 1C).

Figure 1E:
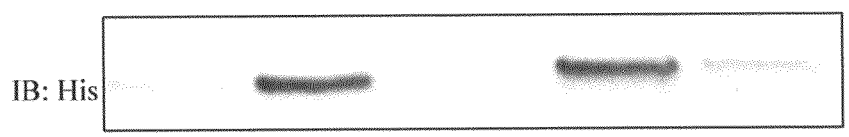

As depicted in FIG. 1A, the N domain contains over 200 amino acid residues. To further map the binding motif in the N domain, the inventors constructed ND2 and ND2 remaining (ND2R) GST fusion proteins as illustrated in FIG. 1A. GST pull-down assay showed that GST-ND2, but not GST-ND2R, bound Src (FIG. 1E).

Further structural analysis of the ND2 reveals that the N-terminus of ND2 is highly unstructural and may undergo induced-fit. Moreover, this domain is also highly exposed and is less important for ATP binding, and thus the catalytic function of the Na/K-ATPase. Thus, to test whether the N-terminus of ND interacts with Src, the inventors constructed two more GST-fusion proteins (ND1 and ND1R), and assessed their binding to Src using GST pull-down assay. As depicted in FIG. 1E, the ND1, but not the ND1R, interacted with Src.

ND1 as a Potent Src Inhibitor can Target to the Na/K-ATPase/Src Complex in Cultured Cells:

To test whether ND1 inhibits Src as did the CD3, the inventors incubated Src with 100 ng soluble GST fusion proteins in the test tube and measured Src pY418 level by Western blot. GST-CD3 was used in the experiment as a positive control and GST-ND was also tested.

As depicted in FIG. 2A, both GST-ND1 and GST-ND were as effective as the positive control in inhibiting Src activity. Moreover, the inhibitory effect of ND1 on Src was dose-dependent ($IC_{50}=50$ nM) (FIG. 2B). To further test whether ND1 can be used as a minigene product to inhibit Src in live cells, the inventors measured Src pY418 level changes in LLC-PK1 cells transfected with different YFP expression vectors. The expression of YFP-ND1, but not YFP, reduced Src activity in cell lysates as did by YFP-ND and YFP-CD3 (FIG. 2C, 2D).

These examples demonstrate the effectiveness of ND1 as a Src inhibitor in cultured cells. To further test whether ND1 can target the plasma membrane Na/K-ATPase/Src complex, the inventors performed the following three sets of experiments.

Figure 3A:
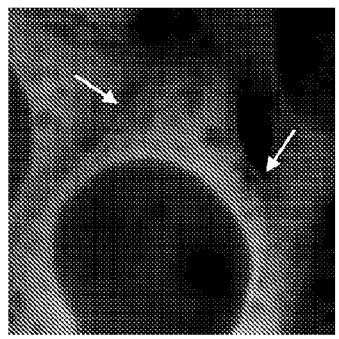
FIGS. 3A-3B: Targeting of YFP-ND1 to the Na/K-ATPase/Src complex in live cells.
Figure 3B:
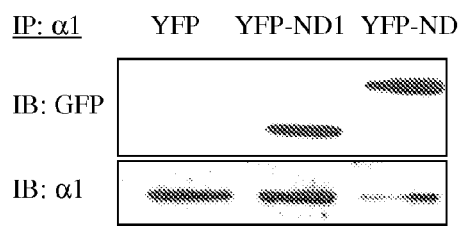

First, as depicted in FIG. 3A, the YFP-ND1 was expressed as a soluble protein. However, the inventors did detect a pool of YFP-ND1 resided near the plasma membrane. Second, to test whether this pool of YFP-ND1 interacts with Src, the inventors co-transfected LLC-PK1 cells with YFP-ND1 and Src-CFP, and then performed FRET analysis. A significant FRET was detected in the cotransfected cells (13.4±2.4%), which showed that YFP-ND1 and the plasma membrane Src-CFP were likely to associate. Finally, when cell lysates were immunoprecipitated by an anti-α1 antibody, the inventors found that YFP-ND1 was co-precipitated (FIG. 3B). Thus, these examples show that YFP-ND1 is most likely capable of interacting with the Na/K-ATPase-associated Src.

Development of NaKtide as a Specific Src Inhibitor:

Since the above data demonstrated that ND1 binds and inhibits Src, the inventors synthesized four 20 mer peptides that cover the entire ND1 and tested which one acts like ND1, capable of inhibiting Src (FIG. 4A).

Based on the crystal structure of Na/K-ATPase, peptide 1 and 2 are un-structural whereas peptides 3 and 4 may form α-helix. As depicted in FIG. 4B, 1 μM peptide 3 caused almost a 100% inhibition of Src while peptide 4 produced a partial inhibition. On the other hand, both peptide 1 and peptide 2 showed no effect. When the dose-response curve was constructed, the inventors showed that peptide 3 was quite potent in inhibiting Src with an $IC_{50}$ of about 70 nM (FIG. 4C), comparable to that of GST-ND1. The peptide 1 had no effect. Since peptide 3 is derived from the Na/K-ATPase, the inventors named it "NaKtide". Because peptide 1 has no effect on Src, it was used as a control. Thus, the inventors named it "C1."

To show that NaKtide acts as an ATP analog as a generic Src inhibitor PP2, the inventors measured its effect on Src in the presence of different concentrations of ATP. As shown in FIG. 4D, changes in ATP concentration from 0.1 to 2 mM did not affect NaKtide-induced Src inhibition.

To probe whether NaKtide is relatively specific to Src, the inventors measured its dose-dependent effect on another Src family kinase Lyn. As shown in FIG. 4E, the NaKtide produced a dose-dependent inhibition of Lyn. However, the $IC_{50}$ is about 2.5 μM, 40 times higher than that of Src inhibition.

To test whether NaKtide affects serine/threonine kinases, the inventors incubated a PKC family kinase cocktail with NaKtide and C1, and then measured for the kinase activity. As shown in FIG. 4F, unlike staurosporine (a non-specific PKC family kinase inhibitor), NaKtide, as well as C1, showed no effect up to 10 μM.

Development of a Cell-Permeable NaKtide as a Ouabain Antagonist:

Recent studies have demonstrated that the coupling of biological molecules to varieties of positively charged cell-penetrating peptides can facilitate their uptake into cultured mammalian cells as well as animal tissues. Accordingly, the inventors synthesized HIV-Tat-NaKtide ("pNaKtide") (see FIG. 5A).

HIV-Tat-P1 (pC1) was also synthesized and used as a control. Meanwhile, after careful review on the Na/K-ATPase α1 sequence, the inventors found an N-terminal polybasic fragment which may facilitate the uptake of NaKtide. The inventors synthesized the Na/K-ATPase α1 N-terminal-NaKtide (A1N-NaKtide). To compare, the inventors also synthesized Penetratin-NaKtide ("AP-NaKtide"). In vitro kinase assay showed that NaKtide was a highly potent Src inhibitor while the control pC1 was inactive (FIG. 5B). Interestingly, addition of HIV-Tat actually increased the potency of the "NaKtide" (peptide 3). The $IC_{50}$ was decreased from 70 nM to about 5 nM. This was also true for AP-NaKtide (data not shown) and A1N-NaKtide (FIG. 5E).

To assess the cell permeability, both pNaKtide and AP-NaKtide were labeled with FITC. As depicted in FIG. 5C, confocal imaging analysis of live cells indicated that pNaKtide, but not NaKtide, was cell-permeable. Maximal loading was achieved after 30 to 60 min of incubation with 1 μM pNaKtide in almost every LLC-PK1 cell in culture. Moreover, unlike YFP-ND1, pNaKtide resided mainly in the plasma membrane with some distribution to the intracellular membrane compartments. On the other hand, when the same experiments were conducted to assess AP-NaKtide, most of AP-NaKtide was in intracellular vesicles. Unlike pNaKtide, very few of AP-NaKtide was detected in the plasma membrane (FIG. 5D). Thus, different tags are likely to direct different intracellular distribution of NaKtide.

To test the effectiveness of pNaKtide as a potential ouabain antagonist, the inventors performed FRET analysis to determine the effect of NaKtide on the formation of Na/K-ATPase/Src receptor complex. LLC-PK1 cells were co-transfected with YFP-α1 and Src-CFP, and then exposed to different concentrations of pNaKtide. The inventors focused on pNaKtide because this conjugate resided mainly in the plasma membrane where the receptor Na/K-ATPase/Src is located.

As depicted in FIG. 6A, both YFP-α1 and Src-CFP were targeted to the plasma membrane. Moreover, a significant FRET was detected in control LLC-PK1 cells. Addition of pNaKtide produced a dose-dependent reduction in overall FRET efficiency (FIG. 6B) as well as the percentage of cells that exhibited detectable FRET (FIG. 6C), indicating that pNaKtide is effective as YFP-ND1 in interacting with the plasma membrane pool of Src, thus blocking the formation of a stable Na/K-ATPase/Src complex. Since significant effect was observed when the cells were exposed to 100 nM to 1 μM pNaKtide, 1 μM pNaKtide was used in the following three sets of experiments to test its effectiveness and specificity as a ouabain antagonist.

First, to assess how pNaKtide affects basal Src and ERK1/2 activity, the inventors exposed LLC-PK1 and the Na/K-ATPase-knockdown TCN23-19 cells to 1 μM pC1 or pNaKtide for different times. Cell lysates were then subjected to Western analysis of active Src and ERK1/2. TCN23-19 cells were derived from LLC-PK1 cells. Knockdown of the Na/K-ATPase in these cells reduces the pool of Src-interacting Na/K-ATPase and thus increases the basal Src and ERK1/2 activity. As depicted in FIG. 7A, pNaKtide caused a 10% inhibition of Src in LLC-PK1 cells. However, this inhibition was not statistically significant (p=0.07). On the other hand, it caused a significant inhibition (over 20%) of basal ERK1/2. This could be explained by that ERK1/2 is a downstream effector of Src. Interestingly, the effect of pNaKtide on Src and ERK in LLC-PK1 cells was much less than those in TCN23-19 cells (FIG. 7A), showing that pNaKtide may selectively target the Na/K-ATPase-interacting pool of Src.

To confirm that the effect of pNaKtide on ERK1/2 is due to its inhibition of Src, the inventors repeated the above experiments in SYF+Src and SYF cells. As shown in FIG. 7B, pNaKtide had no effect on ERK1/2 in SYF cells where Src family kinases (Src, Yes, and Fyn) were knocked out. However, pNaKtide reduced ERK1/2 activity in Src-rescued SYF cells (SYF+Src).

To test whether the plasma membrane residence makes pNaKtide a relative specific inhibitor to the Na/K-ATPaseassociated Src pool, the inventors loaded LLC-PK1 cells with NaKtide in the presence of saponin. As shown in FIG. 9-Table 1, NaKtide, like expression of YFP-ND1, caused more than 50% inhibition of basal Src activity when loaded by saponin. Interestingly, when the effect of AP-NaKtide on basal Src was measured, like pNaKtide, it barely affected the basal Src activity in LLC-PK1 cells.

Second, the inventors measured the effect of pNaKtide in ouabain-induced activation of ERK1/2 in LLC-PK1 cells. This showed that 1 µM pNaKtide completely abolished ouabain-induced ERK1/2 activation in LLC-PK1 cells (FIG. 8A). To confirm that this is not a cell-specific effect, the inventors repeated the same experiments in primary cultures of cardiac myocytes. As shown in FIG. 8B, ouabain-induced activation of ERK1/2 was also blocked by pNaKtide.

The inventors also compared pNaKtide and PP2, a generic Src inhibitor. As shown in FIG. 9—Table 1, both pNaKtide and PP2 have a similar $IC_{50}$ on Src kinase. However, PP2 produced more inhibition on basal Src activity than that of pNaKtide in both LLC-PK1 and cardiac myocytes. Moreover, when cardiac myocytes were stimulated by IGF, PP2, but not pNaKtide, caused a significant inhibition of ERK1/2 activation (FIG. 8C).

Expression of Na/K-ATPase α1 is Reduced in Some Tumor Cell Lines:

Because Src activity is elevated in many types of cancers, the inventors tested whether this elevation is related to the decrease in α1 expression. Western blot analyses confirmed that expression of α1 is indeed reduced in some prostate cancer cell lines (i.e., DU145 and PC-3 cells), breast cancer cell lines (MCF-7), and all tested neuroblastoma cells (FIG. 10A) Immunostaining of Na/K-ATPase α1 also support this notion (FIG. 11B). Moreover, knockdown of Na/K-ATPase α1 in vivo, increased basal Src activity in various tissues including liver (FIG. 10 B). The inventors also found that the α1 expression was more than doubled with an increase in cell density from 50% to 90% whereas active Src was reduced more than 80% in LLC-PK1 cells (FIG. 10C). However, this regulation was lost in DU145 cells, apparently because of defects in both α1 and Src expression (FIG. 10D). When the same experiments were repeated in LNCaP and PC3 cells, we observed essentially the same defect (data not shown).

pNaKtide Inhibits FAK and Reduces Cell Migration:

Because Src is the affector of FAK, a key kinase involved in control of cell migration and thus tumor metastasis, the inventors tested whether pNaKtide can inhibit FAK and tumor cell migration. As depicted in FIG. 11A, pNaKtide caused a time-dependent inhibition of FAK and ERK in TCN23-19 cells where FAK is activated because of Na/K-ATPase-knockdown-induced Src activation. When the effects of pNaKtide were evaluated in DU145 cancer cells, immunostaining with active Src clearly showed a reduction by pNaKtide in both LNCaP and DU145 cells, but not LLC-PK1 cells (FIG. 11B). When the DU145 cell lysates were analyzed by Western blot, the inventors found that pNaKtide reduced not only Src activity in a dose-dependent manner, but also inhibited Src effectors and abolished the expression of Src-regulated oncogene, c-Myc (FIG. 11C). Furthermore, the inventors discovered that pNaKtide produced a dose-dependent inhibition of DU145 migration (FIG. 12).

Expression of ND1 is Sufficient in Killing Cancer Cells where the Expression of Na/K-ATPase is reduced.

Some tumor cells express less Na/K-ATPase and exhibits higher Src activity. The inventors tested whether expression of a Src-inhibiting Na/K-ATPase fragment (ND1) inhibits the cell growth. As depicted in FIG. 13A and FIG. 13B, expression of YFP-ND1 caused cell growth inhibition or cell death in DU145 and MCF-7 cells.

pNaKtide is Effective in Inhibiting Cell Growth in Some Tumor Cell Lines:

The inventors tested whether pNaKtide can be used to inhibit tumor cell growth. As shown in FIG. 14, pNaKtide is effective in blocking the growth of several tumor cell lines including prostate cancer, breast cancer and neuroblastoma.

pNaKtide is Effective in Inhibiting Tumor Growth In Vivo:

The inventors further evaluated the effect of pNaKtide in inhibiting tumor growth in NOD/SCID mice. As depicted in FIG. 15A and FIG. 15B, injection of pNaKtide to NOD/SCID mice bearing xenografted prostate tumors produced a dose-dependent inhibition in both the incidence rate as well as the tumor weight. Quantitative measurement of the tumor volume confirmed the effect of pNaKtide in inhibiting the tumor development is rapid and in a dose-dependent manner (FIG. 15C). Administration of 10 mg/kg pNaKtide resulted in over 75% reduction in both tumor volume and actual tumor weight. And apparently, significant reduction of Src activity was found in the tumors after pNaKtide administration (FIG. 15D).

pNaKtide Inhibits Angiogenesis:

Endothelial cell proliferation is the prerequisite of angiogenesis. As depicted in FIG. 16A, pNaKtide inhibited the proliferation of both HUVEC and HAEC cells in a dose-dependent manner. Moreover, the vessel density of tumors from control mice indicated by CD31 staining was about 10% and pNaKtide treatment reduced the density to about 2.5% (FIG. 16B and FIG. 16C). When the level of angiogenic factor VEGF was assessed, pNaKtide treatment produced significant reduction in the tumor homogenates (FIG. 16D).

DISCUSSION OF THE EXAMPLES

The inventors herein now show a molecular structure of the Na/K-ATPase α1 subunit that interacts and inhibits Src. The inventors have also engineered a novel peptide Src inhibitor that can target the Na/K-ATPase/Src receptor complex and thus function as an effective ouabain antagonist in cultured cells.

Identification of NaKtide as a New Class of Src Inhibitor:

The CD3 of Na/K-ATPase al subunit consists of both N and P domains. The inventors have shown that CD3 binds the Src kinase domain and inhibits Src kinase activity in vitro. Based on the newly released crystal structure of Na/K-ATPase, the N domain is exposed, whereas the P domain is relatively close to the membrane.

The inventors now show that the N domain binds and inhibits Src. Interestingly, it is known that the less structural N-terminus of SERCA N domain interacts with phospholamban. The inventors now demonstrate that the ND1 (FIG. 2), the first 50 amino acid residues of the α1 N domain, inhibits Src. However, further mapping analyses reveal that the corresponding phospholamban-binding domain in ND1 (peptide 2, see FIG. 4A) actually had no effect on Src kinase activity.

Instead, peptide 3 and peptide 4 showed strong inhibitory effect on Src. Based on the crystal structure as well as NMR data, both peptides possessed a helix structure, suggesting that helix/helix interaction between the ND1 and the Src kinase may be responsible for the Na/K-ATPase-induced Src inhibition. Literature review reveals that several endogenous proteins interact and inhibit Src. Noteworthy are RACK1 and WASP. While RACK1 inhibits Src via its interaction with the SH2 domain, WASP does so by binding to the Src kinase domain. However, no detailed structural information is available for further comparison.

Like inhibitors of other tyrosine kinases, most Src inhibitors are ATP mimetics. When the ATP dependence was assessed, the inventors found that changes in ATP concentration did not affect NaKtide-induced Src inhibition. Moreover, it is unlikely that NaKtide acts as a substrate Src inhibitor since the peptide does not contain Tyr residue. Furthermore, limited structural analyses show that NaKtide interacts with N-lobe, but not the substrate pocket-containing C-lobe, of the kinase domain (Li and Xie, unpublished data). Thus, NaKtide represents a novel class of Src inhibitor.

As a Src inhibitor, both NaKtide and ND1 are potent. The $IC_{50}$ is close to 50 nM, comparable to most of reported Src inhibitors. Finally, when the effects of NaKtide on other kinases were assessed, the inventors found that NaKtide appears to be relatively specific to Src. NaKtide showed no effect on PKC family of kinases. Its effect on ERK1/2 depends on the expression of Src, indicating that it is not an ERK inhibitor but can affect ERK signaling by inhibiting Src. This is consistent with the fact that ERK1/2 are well-known effectors of Src kinase. Interestingly, although NaKtide inhibits Lyn, another Src family kinase, it exhibits much lower potency toward Lyn than Src (FIG. 4E).

Development of pNaKtide as a Specific Ouabain Antagonist:

Transient transfection assays indicate that YFP-ND1 resided as a soluble protein and inhibited basal Src as effective as PP2 (FIG. 3A and FIG. 9—Table 1). Moreover, a small fraction of YFP-ND1 was detected in the plasma membrane. Both FRET and immunoprecipitation assays showed that this plasma membrane-targeted YFP-ND1 disrupted the interaction between the Na/K-ATPase and Src (FIG. 3B and FIG. 6A). Taken together, these discoveries now show that ND1 and its derivative NaKtide may be used as an effective Src inhibitor or a relatively specific ouabain antagonist depending on its cellular distribution.

This is supported by the experimental evidence where the inventors found that loading NaKtide by saponin into LLC-PK1 cells caused about 60% inhibition of basal Src activity as did by PP2 or expression of YFP-ND1. Also, it is demonstrated herein that tagging a positively charged leader peptide, such as HIV-Tat to NaKtide, made it readily cell permeable. Moreover, confocal imaging analyses showed that a majority of pNaKtide resided in the plasma membrane and had much less effect on basal Src activity in both LLC-PK1 and cardiac myocytes. Interestingly, when pNaKtide was applied to TCN23-19 cells where the pool of Src-interacting Na/K-ATPase is depleted, in contrast to that in LLC-PK1 cells, pNaKtide caused about 50% inhibition of cellular Src activity. As such, the plasma membrane-targeted pNaKtide is now believed by the inventors herein to have a relatively specific effect on the Na/K-ATPase-interacting pool of Src.

The pNaKtide was very effective in blocking the formation of Na/K-ATPase/Src receptor complex (FIG. 6B). In accordance, ouabain-induced activation of ERK1/2 in LLC-PK1 cells was completely abolished by 1 μM pNaKtide (FIG. 8A). Moreover, pNaKtide also resided mainly in the plasma membrane in cardiac myocytes and was effective in inhibiting ouabain-induced activation of ERK1/2 (FIG. 8B).

The specificity of pNaKtide toward the Na/K-ATPase/Src complex was further demonstrated by experiments showing that PP2, but not pNaKtide, caused a significant inhibition of IGF-induced ERK1/2 activation (FIG. 8C).

Although ouabain and other CTS have been considered only as drugs since their discovery, recent studies have identified both ouabain and marinobufagenin (MBG) as endogenous steroids whose production and secretion are regulated by multiple physiological stimuli including ACTH and angiotensin II. Moreover, they are found to play an important role in the regulation of renal salt handling, vascular and cardiac contractions. Pathologically, they are likely to be involved in cardiovascular remodeling seen during chronic renal failure and the pathogenesis of autosomal dominant polycystic kidney disease (ADPKD) by stimulating the proliferation of renal epithelial cells.

Therefore, the pNaKtide can be useful in determining the physiology, as well as to probe the pathological significance, of Na/K-ATPase and endogenous CTS. This is of particular importance since it is now believed that physiologically relevant doses of ouabain and MBG are sufficient to stimulate Src and its down-stream protein kinase cascades in the heart and kidney. Moreover, PST 2238, an ouabain antagonist, has been demonstrated as an effective anti-hypertensive drug. Therefore, pNaKtide can also be useful as a new therapeutics for cardiovascular diseases where the Na/K-ATPase/Src receptor is over-stimulated.

Identification of key amino acid residues in NaKtide that bind and inhibit Src, where in the kinase domain NaKtide binds to, and how the binding inhibits Src can be useful, only to reveal the molecular mechanism of Na/K-ATPase-mediated Src regulation, but to assess whether this regulation is isoform-specific.

It is to be noted that four different α subunits have been identified. Moreover, Src family kinases include at least nine members. Interestingly, although Src and Lyn are highly homologous, NaKtide appears to be more potent toward Src than Lyn. Thus, it is likely that this regulation could be isoform-specific. Also, determining whether NaKtide affects kinases other than PKC, ERK and Src can be further useful.

The AP-NaKtide and A1N-NaKtide resided mainly in intracellular vesicles. Like pNaKtide, it also had almost no effect on basal Src activity. As such, determining whether AP-NaKtide or A1N-NaKtide can block ouabain-induced ERK1/2 activation can also be useful. Moreover, AP-NaKtide and A1N-NaKtide may have a relative specific effect on endocytosis, exocytosis or vesicle recycling since Src is known to play a role in these events. Further, assessment of the ability of pNaKtide as a ouabain antagonist in intact animals or isolated organs can provide further proof of the usefulness of the novel NaKtide.

Development of pNaKtide as a potential anti-cancer therapeutics: Many tumors have elevated Src activity. Both in vitro and in vivo studies have demonstrated that cellular Src activity is inversely correlated with the amount of Na/K-ATPase. Thus, supplement of Src-inhibiting Na/K-ATPase or its equivalent (ND1 or pNaKtide) may be useful for reducing the tumor growth. Moreover, because Src controls FAK activity that is required for tumor metastasis, the Na/K-ATPase and its equivalent may also be effective in preventing tumor metastasis. Consistently, the inventors demonstrate that many tumor cell lines express less Na/K-ATPase and have higher Src activity (FIG. 10 and FIG. 11). Rescuing these cells with YFP-ND1 or pNaKtide is effective in inhibiting the growth of these tumor cells (FIG. 13 and FIG. 14). Furthermore, pNaKtide inhibits FAK and blocks tumor cell migration in vitro (FIG. 11 and FIG. 12). Also, in vivo studies show that IP injection of pNaKtide can block the growth of xenografted prostate tumor in NOD/SCID mice (FIG. 15). Inhibition of Src in tumors may be involved in the regulation of angiogenesis by pNaKtide (FIG. 16), which will further limit the nutrients supply for the tumor growth. Taken together, these findings indicate that pNaKtide may be useful as an anti-cancer therapeutic agent.

DEFINITIONS

The abbreviations used are: A domain, activation domain; CD2, second cytosolic domain; CD3, third cytosolic domain; CTS, cardiotonic steroids; EYFP, enhanced yellow fluorescent protein; ERK, extracellular signal-regulated protein kinase; FAK, focal adhesion kinase; FRET, fluorescence resonance energy transfer; GST, glutathione-S-transferase; IGF-1, insulin-like growth factor 1; MAPK, mitogen-activated protein kinase; N domain, nucleotide-binding domain; P domain, phosphorylation domain; PI3K, phosphatidylinositol 3-kinase; PKC, protein kinase C; PLC, phospholipase C; PP2,4-amino-5-[4-chlorophenyl]-7-[t-butyl]pyrazolo[3,4-d]pyrimidine; SERCA, sarcoplasmic reticulum Ca-ATPase.

```
Sequence Listings:
peptide 1
                                                [SEQ ID NO: 1]
. . . MTVAHMWFDNQIHEADTTEN peptide 2
                                                [SEQ ID NO: 2]
. . . IHEADTTENQSGVSFDKTSA peptide 3
                                                [SEQ ID NO: 3]
. . . SATWLALSRIAGLCNRAVFQ peptide 4
                                                [SEQ ID NO: 4]
. . . ALSRIAGLCNRAVFQANQEN ND1
                                                [SEQ ID NO: 5]
. . . LTQNRMTVAHMWFDNQIHEADTTENQSGVSFDKTSATWLALSR
IAGLCNRAVFQANQEN pC1
                                                [SEQ ID NO: 6]
. . . G R K K R R Q R R R P P Q M T V A H M W F D
N Q I H E A D T T E N pNaKtide
                                                [SEQ ID NO: 7]
. . . G R K K R R Q R R R P P Q S A T W L A L S R
I A G L C N R A V F Q AP-NaKtide
                                                [SEQ ID NO: 8]
. . . R Q I K I W F Q N R R M K W K K S A T W L A
L S R I A G L C N R A V F Q A1N-NaKtide
                                                [SEQ ID NO: 9]
. . . K K G K K G R K S A T W L A L S R I A G L C
N R A V F Q
```

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

---

What is claimed is:

1. A composition of matter comprising an isolated amino acid peptide consisting of the sequence KKGKKGKK-SATWLALSRIAGLCNRAVFQ [SEQ ID NO:9].

2. The composition of claim 1, further comprising a therapeutically acceptable excipient.

3. The composition of claim 1, wherein the peptide is capable of Src inhibition.

4. The composition of claim 1, which further comprises at least one additional therapeutic composition useful to treat a disease selected from the group consisting of: cancer; vascular disease; cardiovascular disease; heart disease; bone disease; prostate cancer; breast cancer; neuroblastoma; cardiac hypertrophy; tissue fibrosis; congestive heart failure; ischemia/reperfusion injury; and osteoporosis.

5. The composition of claim 1, further comprising at least one additional therapeutic composition to treat cancer.

6. The composition of claim 1, wherein the peptide is capable of a cellular process selected from the group consisting of: antagonizing a CTS-induced protein kinase cascade; Src inhibition; Na/K-ATPase mimic; Lyn inhibition; ouabain antagonism; FAK/ERK1/2 inhibition; anti-angiogenesis; and inhibition of cell growth.

7. The composition of claim 1, further comprising a second compound bound with the amino acid sequence, wherein the second compound is selected from the group consisting of: chemotherapeutic drug; toxin; immunological response modifier; enzyme; and radioisotope.

* * * * *